(12) United States Patent
Kusaka

(10) Patent No.: US 9,125,604 B2
(45) Date of Patent: Sep. 8, 2015

(54) ELECTROCHEMICAL SENSOR

(75) Inventor: Yasuhide Kusaka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1148 days.

(21) Appl. No.: 13/110,563

(22) Filed: May 18, 2011

(65) Prior Publication Data

US 2012/0130213 A1    May 24, 2012

(30) Foreign Application Priority Data

May 19, 2010 (JP) ................ 2010-115793
May 18, 2011 (JP) ................ 2011-110947

(51) Int. Cl.
*A61B 5/05* (2006.01)
*A61B 5/145* (2006.01)
*A61B 5/1486* (2006.01)
*A61B 5/00* (2006.01)

(52) U.S. Cl.
CPC .......... *A61B 5/14532* (2013.01); *A61B 5/14865* (2013.01); *A61B 5/0002* (2013.01)

(58) Field of Classification Search
CPC .............. A61B 5/145; A61B 5/14503; A61B 5/14532; A61B 5/1468; A61B 5/1473
USPC ........................ 600/345-347, 365
See application file for complete search history.

(56) References Cited

U.S. PATENT DOCUMENTS

| | | | |
|---|---|---|---|
| 2,402,306 A * | 6/1946 | Turkel ............. | 604/174 |
| 4,628,928 A | 12/1986 | Lowell | |
| 4,771,772 A | 9/1988 | DeWitt | |
| 5,628,312 A | 5/1997 | Musinski | |
| 5,954,643 A | 9/1999 | VanAntwerp et al. | |
| 6,134,461 A | 10/2000 | Say et al. | |
| 6,368,141 B1 | 4/2002 | VanAntwerp et al. | |
| 6,973,706 B2 | 12/2005 | Say et al. | |
| 7,003,340 B2 | 2/2006 | Say et al. | |
| 7,494,465 B2 * | 2/2009 | Brister et al. ............. | 600/309 |
| 2002/0119711 A1 | 8/2002 | VanAntwerp et al. | |
| 2003/0057952 A1 | 3/2003 | Derr | |
| 2005/0234312 A1 | 10/2005 | Suzuki et al. | |
| 2008/0064944 A1 | 3/2008 | VanAntwerp et al. | |

(Continued)

FOREIGN PATENT DOCUMENTS

| | | |
|---|---|---|
| EP | 1736763 A1 | 12/2006 |
| JP | 2931744 | 5/1999 |

(Continued)

OTHER PUBLICATIONS

The extended European Search Report issued on Mar. 1, 2013, which corresponds to EP Application No. 11166805.9 and is related to U.S. Appl. No. 13/110,563.
The extended European Search Report issued on Mar. 1, 2013, which corresponds to EP Application No. 11166805.9-1559/2388584 and is related to U.S. Appl. No. 13/110,563.

(Continued)

*Primary Examiner* — Michael D'Angelo
(74) *Attorney, Agent, or Firm* — Studebaker & Brackett PC

(57) ABSTRACT

An electrochemical sensor includes a base plate including one end portion and another end portion, an electrode portion formed on the one end portion of the base plate, a connecting portion, formed on the another end portion of the base plate, for electrically connecting the electrode portion to a monitoring instrument, and an attaching portion formed on the another end portion, the attached portion being employed for attaching the another end portion to the monitoring instrument in a state where the one end portion is enabled to swing relatively to the monitoring instrument.

15 Claims, 12 Drawing Sheets

(56) References Cited

U.S. PATENT DOCUMENTS

2008/0308523 A1    12/2008    Krulevitch et al.
2009/0076360 A1    3/2009    Brister et al.
2010/0015006 A1    1/2010    Hsu

FOREIGN PATENT DOCUMENTS

| | | |
|---|---|---|
| JP | H11-508157 A | 7/1999 |
| JP | 2002-503988 A | 2/2002 |
| JP | 2003-524159 A | 8/2003 |

OTHER PUBLICATIONS

Communication pursuant to Article 94(3) EPC issued by the European Patent Office on Dec. 19, 2014, which corresponds to European Patent Application No. 11166805.9-1559 and is related to U.S. Appl. No. 13/110,563.

An Office Action; "Notice of Reasons for Rejection," issued by the Japanese Patent Office on Jan. 13, 2015, which corresponds to Japanese Patent Application No. 2011-110947 and is related to U.S. Appl. No. 13/110,563.

* cited by examiner

ELECTROCHEMICAL SENSOR

This application claims the benefits of priority of the prior Japanese Patent Application No. 2010-115793 filed on May 19, 2010 and the Japanese Patent Application No. 2011-110947 filed on May 18, 2011, the entire contents of which are incorporated herein by reference.

BACKGROUND OF THE INVENTION

The present invention relates to an electrochemical sensor which is indwelled subcutaneously in human being and an animal and continuously measures (monitors) a physical quantity of components within a living organism.

An RT-CGM (Real-Time Continuous Glucose Monitoring) apparatus performs a Continuous Glucose Monitoring (CGM) process for continuously measuring (monitoring) a concentration of glucose contained in a subcutaneous interstitial liquid by employing a biosensor, which has an electrode and an enzyme reacting on the glucose, indwelled subcutaneously.

The RT-CGM device includes, as a basic configuration, a sensor unit and a data receiver which performs data communications with the sensor unit. The sensor unit includes a biosensor and a measuring (monitoring) instrument to which the biosensor is attached. A part of the biosensor is fitted in a fixed state within a housing of the monitoring instrument.

The biosensor is formed in a sheet-like or board like shape. Also, the biosensor has a one end portion formed on a plurality of electrodes and another end portion fixed within the housing for the monitoring instrument. The biosensor is fitted in the monitoring instrument in a state where the one end portion thereof protrudes from the housing for the monitoring instrument. The other end portion of the biosensor is inserted into a living organism of an examinee and is indwelled subcutaneously when the monitoring instrument is attached to the examinee for monitoring the glucose.

Electronic components composing a sensor control unit and a data transmitter are disposed within the housing for the monitoring instrument. The sensor control unit is electrically connected to a plurality of electrodes provided on the biosensor. The sensor control unit controls application of a voltage to between the plurality of electrodes and detection of an inter-electrode current (called a response current) derived from enzyme reaction caused by this voltage application. The data transmitter converts, e.g., a value of the detected response current into a predetermined data communication format and transmits the thus-converted data to a data receiver.

The data receiver includes an computing unit (computer) which computes a glucose concentration by a known technique such as monitoring the glucose concentration in a way that uses a calibration curve on the basis of the response current value received from the data transmitter of the monitoring instrument, and a display device which displays the computed result. The computed result (glucose concentration) is displayed by the display device, thereby the glucose concentration in an interstitial liquid is presented.

The RT-CGM device is capable of continuously acquiring the response current while the biosensor is kept indwelling subcutaneously. Therefore, the data transmitter transmits anytime the response current value per predetermined time (unit time) to the data receiver, and the display device of the data receiver may continuously display time-based variations of the glucose concentration.

There has hitherto existed a biosensor of which the other end portion is formed with portions (called contact pads) serving as electric contacts between the plurality of electrodes and the electronic components within the housing for the monitoring instrument (refer to, e.g., Patent document 1). The contact pad is formed on a per-electrode basis. The other end portion of the biosensor is fixed within the housing in the way of being interposed between components or portions within the housing. On this occasion, the respective terminals (contacts) of the electronic components installed within the housing contact the contact pads, thereby connections between the individual electrodes and the electronic components is established.

[Patent document 1] U.S. Pat. No. 6,973,706 (FIG. 2)

The one end portion of the biosensor is indwelled subcutaneously in the examinee when monitoring the response current, and hence external force is applied depending on how the examinee moves. According to the conventional technology described above, the other end portion is fixed by interposing the other end portion of the biosensor in interior of the housing. Thus, the conventional technology is not structured to absorb the external force applied to the one end portion of the biosensor through the movement of the biosensor. Therefore, there is a possibility that tissues around the one end portion are damaged.

Moreover, if the external force is applied to the one end portion indwelled subcutaneously due to a muscular movement, force acting in a rotating direction occurs on the flat surface of the other end portion with the result that the one end portion deviates in position, whereby the contact between the contact pads and the terminals might lose its preferable state.

SUMMARY OF THE INVENTION

It is an object of the present invention to provide a technology capable of properly absorbing the external force applied to the electrochemical sensor.

It is another object of the present invention to provide a technology capable of keeping a preferable state of the electric connection even when the external force is applied to the one end portion of the electrochemical sensor.

The present invention adopts the following configurations in order to accomplish the above objects. Namely, a first aspect of the present invention is an electrochemical sensor including:

a base plate including one end portion and another end portion; an electrode portion formed on the one end portion of the base plate; a connecting portion, formed on the another end portion of the base plate, for electrically connecting the electrode portion to a monitoring instrument; and an attaching portion, formed on the another end portion, the attaching portion being employed for attaching the another end portion to the monitoring instrument in a state where the one end portion is enabled to swing relatively to the monitoring instrument.

According to the first aspect of the present invention, the electrochemical sensor is attached to the monitoring instrument via the attaching portion in the state where the base plate swings relatively to the monitoring instrument. Hence, the electrochemical sensor swings when the external force is applied to the electrochemical sensor. Therefore, the external force may be absorbed. Thus, the first aspect of the present invention prevents analyte organisms around the one end portion from damages.

The first aspect of the present invention may adopt a configuration that the attaching portion includes a through-hole into which a shaft provided on the monitoring instrument is inserted, and the one end portion swings around the shaft.

The first aspect of the present invention may adopt a configuration that the attaching portion includes a notched portion formed in the another end portion of the base plate. The notched portion includes: a first portion having a diameter corresponding to an outside diameter of the shaft provided on the monitoring instrument; and a second portion communicating the first portion with an outer edge of the another end portion and having a gap that is smaller than the outside diameter of the shaft.

The first aspect of the present invention may adopt a configuration that the attaching portion includes two recessed portions formed coaxially in an electrode forming surface of the base plate and in a reverse surface to the electrode forming surface, wherein respective ends of two shafts or protruded portions provided within the monitoring instrument and disposed in a face-to-face state on a same straight line are inserted into the two recessed portions when the electrochemical sensor is attached to the monitoring instrument.

The first aspect of the present invention may adopt a configuration that the attaching portion includes two protruded portions formed coaxially on an electrode forming surface of the base plate and on a reverse surface to the electrode forming surface, wherein the respective protruded portions are inserted into two recessed portions provided within the monitoring instrument.

Alternatively, the attaching portion in the first aspect may be configured to include: a recessed portion, formed on one of an electrode forming surface of the base plate and a reverse surface to the electrode forming surface, into which a protruded portion provided within the monitoring instrument is inserted; and a protruded portion formed, coaxially with the recessed portion, on another one of the electrode forming surface and the reverse surface and inserted into a recessed portion provided within the monitoring instrument.

In a case where the first aspect of the present invention has the through-hole, the first aspect may adopt configuration that the through-hole is formed on a central line of the one end portion of the base plate in a plane view.

In a case where the first aspect of the present invention has the notched portion, the first aspect may adopt a configuration that a center of the first portion included in the notched portion is provided on a center line of the one end portion of the base plate in a plane view.

In a case where the first aspect of the present invention has the two recessed portions, the first aspect may adopt a configuration that the two recessed portions are provided on a center line of the one end portion of the base plate in a plane view.

In a case where the first aspect of the present invention has the two protruded portions, the first aspect may adopt a configuration that the two protruded portions are provided on a center line of the one end portion of the base plate in a plane view.

Further, the first aspect may adopt a configuration that the attaching portion includes at least two through-holes, each of which has a circular arc shape, formed on a same circumference in the another end portion, wherein at least two shafts provided within the monitoring instrument are inserted into the through-holes.

Moreover, the first aspect may adopt a configuration that the another end portion is formed in a circular shape and mounted on a mounting portion provided within the monitoring instrument, wherein the mounting portion includes: a bottom face; and a sidewall erected from the bottom face and having a cylindrical peripheral face corresponding to the outside diameter of the another end portion.

The first aspect may adopt a configuration that the connecting portion electrically connects the electrode portion to the monitoring instrument via a slip ring provided within the monitoring instrument. This configuration being taken, it is feasible to keep a proper state of the connection between the monitoring instrument and the electrode even when the base plate swings.

The electrochemical sensor according to the first aspect may adopt a configuration that the electrochemical sensor includes a lead portion connected to the electrode portion and is provided on the base plate in a way of extending over to the another end portion from the one end portion, and the lead portion is, with the monitoring instrument and the electrode portion being electrically connected via the connecting portion, provided over a range of relatively moving on the another end portion corresponding to a swing of the one end portion. According to the above-configuration, it is possible to keep a proper state of connection between the monitoring instrument and the electrode portion even when the base sheet swings.

The electrode portion in the first aspect may include a plurality of electrodes. For example, at least two or more electrodes, as the plurality of electrodes, are formed on the one end portion of the base plate. Further, the electrode portion may include a reactive substance layer which reacts on a specified substance and generates an electric current when reacting thereon. When the electrode portion includes the plurality of electrodes, the reactive substance layer may be formed on at least one of the plurality of electrodes. Alternatively, the reactive substance layer may be formed in a manner that extends over the two or more electrodes and may be also formed for every two or more electrodes.

The one end portion may be constructed to be embedded subcutaneously.

The electrochemical sensor in the first aspect may be configured so that, in a state where the base plate is viewed in plane, the one end portion includes a first side and a second side each extending in a longitudinal direction of the electrochemical sensor and having a face-to-face relation with each other, while the another end portion includes a third side and a fourth side each extending in the longitudinal direction and having the face-to-face relation with each other, and at least one group of sides among a group of the first and second sides and a group of the second and fourth sides, are joined in a way that interposes at least another side in a direction intersecting the longitudinal direction.

Further, the electrochemical sensor in the first aspect may be configured so that a part or whole of an outer edge shape of the another end portion is formed by curves.

A second aspect of the present invention is a monitoring instrument attached with the electrochemical sensor according to the first aspect and monitoring a signal given from the electrode, the monitoring instrument including: a monitoring-instrument-sided connecting portion to electrically connect the connecting portion to the monitoring instrument; and an attached portion to hold the another end portion in a state where the one end portion swings relatively to the monitoring instrument.

In the second aspect, the attached portion may include a shaft to which the electrochemical sensor is attached, the shaft becoming a center of swing of the one end portion.

In the second aspect, the attached portion may include the attached portion which includes two shafts or two protruded portions disposed in a face-to-face state on a same straight line, and ends of the shafts or the protruded portions are inserted respectively into two recessed portions formed coaxially in an electrode forming surface and in a reverse surface to the electrode forming surface of the electrochemical sensor.

In the second aspect, the attached portion may include two recessed portions into which two protruded portions, which are formed coaxially on an electrode forming surface and on a reverse surface to the electrode forming surface of the electrochemical sensor, are inserted. In this case, the recessed portions and the protruded portions may be provided on a center line of the one end portion of the base plate in a plane view.

In the second aspect, the attached portion may include at least two shafts inserted into at least two through-holes, each of which has circular arc shape, formed on a same circumference in the another end portion of the electrochemical sensor. The attached portion may also include: a protruded portion inserted into a recessed portion, which is formed on one of an electrode forming surface of the electrochemical sensor and a reverse surface to the electrode forming surface; and a recessed portion into which a protruded portion, which is formed, coaxially with the recessed portion, on another one of the electrode forming surface and the reverse surface, is inserted.

Further, the second aspect may adopt a configuration that the other end portion of the electrochemical sensor is formed in a circular shape, the attached portion includes a mounting portion including a bottom face and a sidewall erected from the bottom face and having a cylindrical peripheral face corresponding to an outside diameter of the another end portion, and the another end portion is mounted on the bottom face.

Still further, the second aspect may adopt a configuration that the monitoring-instrument-sided connecting portion includes a slip ring which comes into contact with the connecting portion of the electrochemical sensor in a state where the electrochemical sensor is held by the attached portion.

Yet further, the second aspect may adopt a configuration that the monitoring-instrument-sided connecting portion keeps a contact state with the connecting portion of the electrochemical sensor in an swing range of the one end portion in a state where the electrochemical sensor is held by the attached portion.

According to the present invention, it is possible to provide the technology capable of properly absorbing the external force applied to the electrochemical sensor.

Further, according to the present invention, it is possible to provide the technology capable of keeping the preferable state of the electric connection even when the external force is applied to the electrochemical sensor.

BRIEF DESCRIPTION OF THE DRAWINGS

FIG. 18A is a view schematically illustrating a state in which a principal portion for connecting the electrochemical sensor (the glucose sensor) secured to the shaft to the monitoring instrument by use of the slip ring, is viewed sideways; and FIG. 18B is a view schematically showing a state in which the principal portion shown in FIG. 18A is viewed in plane from above.

DETAILED DESCRIPTIONS OF THE EMBODIMENTS

Embodiments of the present invention will hereinafter be described with reference to the drawings. Configurations in the following embodiments are exemplifications, and the present invention is not limited to the configurations in the embodiments.

First Embodiment

Figure 1:
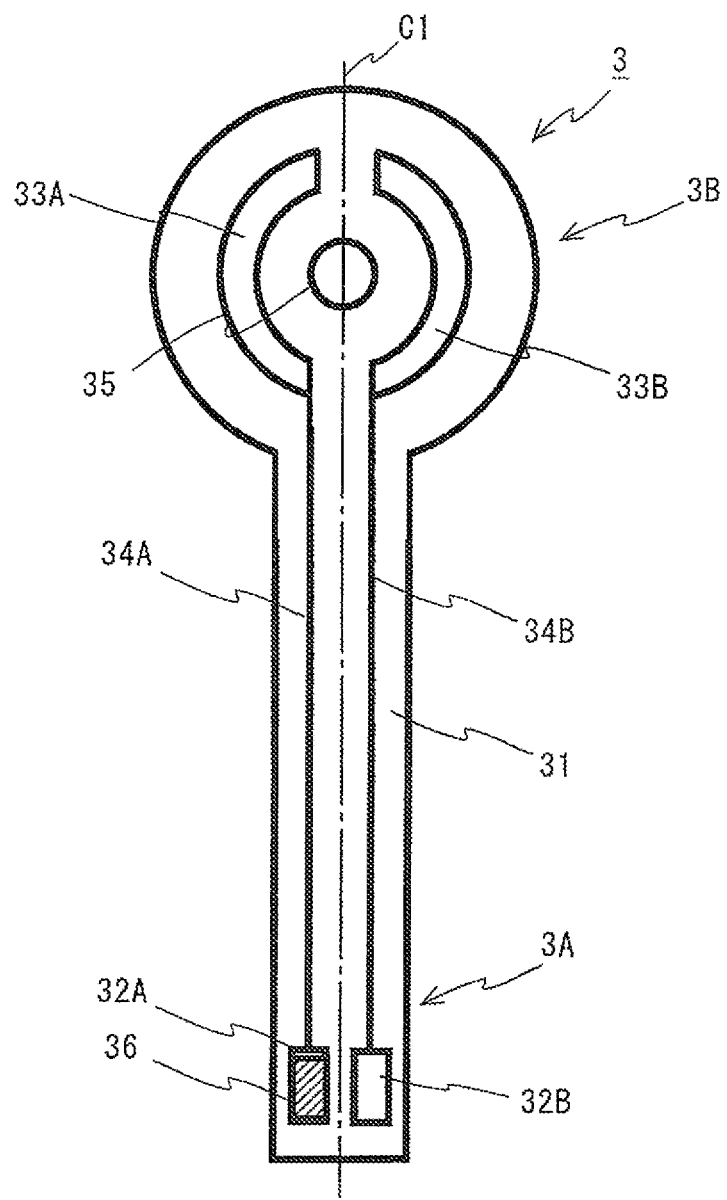
FIG. 1 is a view showing an example of a configuration of an electrochemical sensor according to a first embodiment of the present invention.
Figure 2:
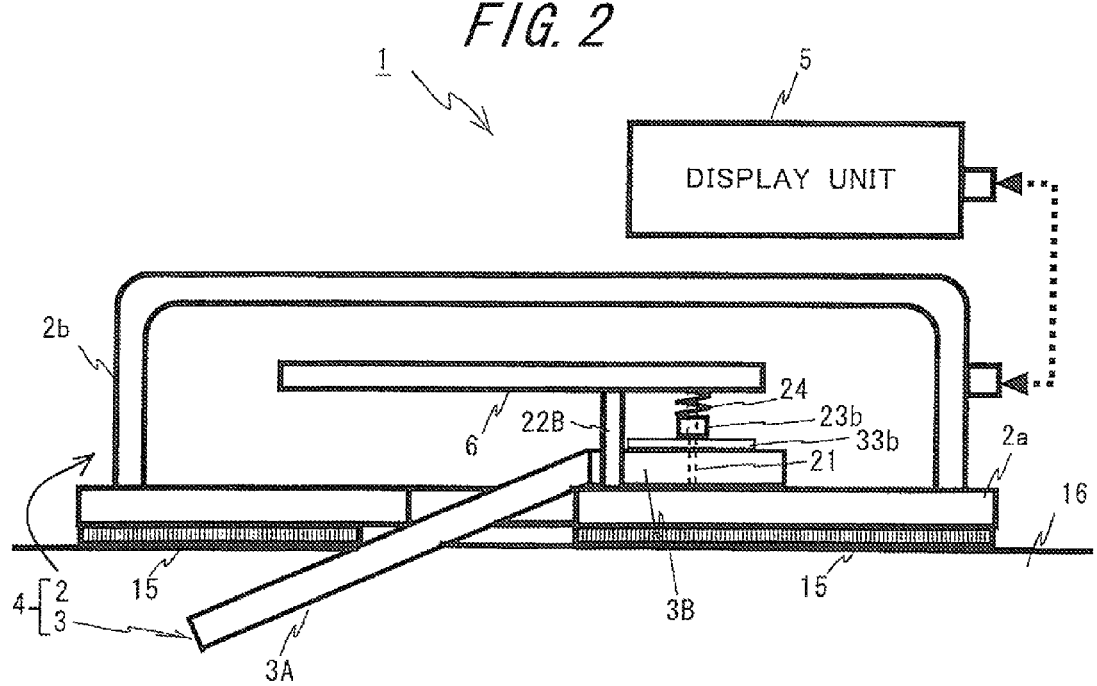
FIG. 2 is a view illustrating an RT-CGM device including a monitoring instrument to which the electrochemical sensor shown in FIG. 1 is applied and a display unit.
Figure 3:
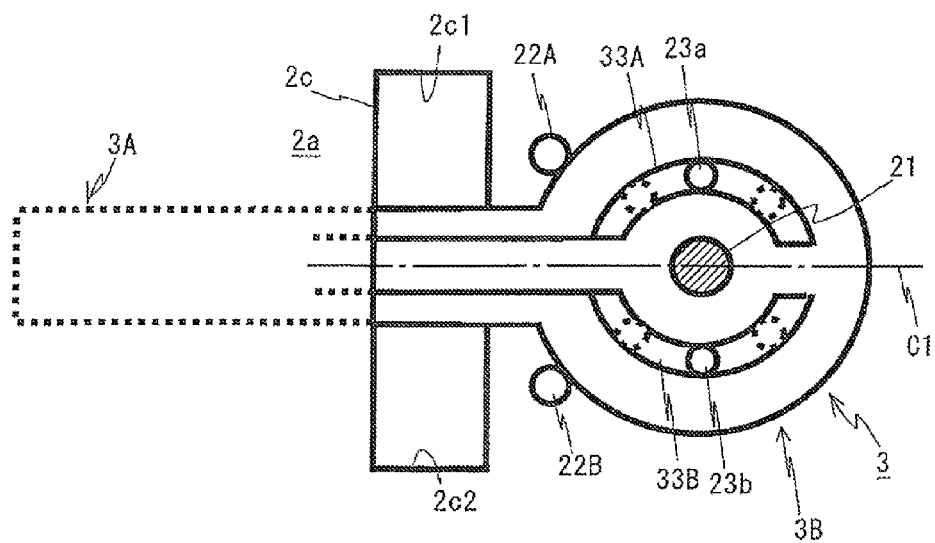
FIG. 3 is a view schematically showing a state where the electrochemical sensor attached to the monitoring instrument is viewed in plane from above.

FIG. 1 is a view showing an example of a configuration of an electrochemical sensor according to a first embodiment of the present invention. FIG. 2 is a view illustrating an RT-CGM apparatus, to which the electrochemical sensor illustrated in FIG. 1 is applied, including a monitoring apparatus and a display unit. FIG. 3 schematically shows a state where the electrochemical sensor attached to the monitoring instrument is viewed in plane from above.

An RT-CGM apparatus (which will hereinafter be simply termed a monitoring apparatus) 1 shown in FIG. 2 is used for automatically continuously monitoring (measuring), as a physical quantity of a specified ground substance in a body fluid, a glucose concentration in an interstitial liquid of a human being and an animal (which are generically referred to as an examinee). The monitoring apparatus 1 includes a sensor unit 4 including a monitoring instrument 2 and an electrochemical sensor 3, and a display unit 5 serving as a data receiver which performs communications with the sensor unit 4.

A housing of the monitoring instrument 2 has a base plate 2a and a cover 2b which covers the base plate 2a. The base plate 2a and the cover 2b are firmly joined into one integral unit. An inner space of the housing, which is defined by the base plate 2a and the cover 2b, accommodates at least a substrate 6 on which electronic components configuring a control computer and a communication device are installed, and a part of the electrochemical sensor 3.

The housing for the monitoring instrument 2 is constructed in a manner that uses materials having a water proofing property or a water resistance. For example, at least the cover 2b (and the base plate 2a as the case may arise) is composed of at least one material such as a metal and a synthetic resin having an extremely low permeability. The synthetic resin may involve applying, for example, polypropylene.

The electrochemical sensor 3 detects a specified detected substance (analyte) by utilizing electrochemical reaction, and a biosensor is applied to the embodiments. The biosensor, which is employed as an element that detects an analyte of a living organism or a material derived from the living organism, continuously monitors and detects the analyte.

The electrochemical sensor 3 in the embodiments is employed for continuously monitoring a glucose concentration in an interstitial liquid. The electrochemical sensor (biosensor) 3 will therefore be referred to as a "glucose sensor 3".

As illustrated in FIG. 1, the glucose sensor 3 is formed with a sheet-like or a board-like shape having one end portion 3A and another end portion 3B. To be specific, the glucose sensor 3 includes a base plate 31, at least one electrode (electrodes 32A and 32B) formed at the one end portion 3A on one surface of the base plate 31, and contact pads 33A and 33B formed at the other end portion 3B. The glucose sensor 3 also includes lead portions 34A and 34B formed on the base plate 31 so as to extend from the other end portion 3B to the one end portion 3A, respectively. The lead portions 34A and 34B respectively connect the electrodes 32A, 32B with the contact pads 33A, 33B.

The base plate 31 is a film-shaped base plate constructed by applying thermoplastic resins such as polyethyleneterephthalate (PET), polypropylene (PP) and polyethylene (PE) and resins such as a polyimide resin and an epoxy resin having no harmful effect in the human body but a proper insulating property and flexibility.

In the example illustrated in FIG. 1, an outer periphery shape of the other end portion 3B of the base plate 31 is formed in a circular shape, while outer peripheries of an intermediate portion and the one end portion 3A are formed in an elongate rectangle, whereby the whole base plate 31 has an outer periphery shape formed by joining a circle and a rectangle together in bilateral symmetry with respect to a center line C1.

Metal layers are formed on the one surface of the base plate 31. One of the metal layers is employed as the electrode 32A, the lead portion 34A and the contact pad 33A. Another one of the metal layers is employed as the electrode 32B, the lead portion 34B and the contact pad 34A. These metal layers are formed, for example, by forming one metal layer that is grown by physical-vapor-depositing (PVD, e.g., sputtering) or by chemical-vapor-depositing (CVD) a metal such as gold and platinum and divide of the one metal layer by using laser-based trimming.

A carbon layer (unillustrated) formed by screen-printing, e.g., a carbon paste is stacked on the metal layer partly making up the electrode 32A, thus composing the electrode 32A from the metal layer and the carbon layer. An enzyme-immobilized layer 36 (a reactant layer) immobilized with an enzyme reacting on the glucose is formed on the carbon layer.

With this arrangement, the electrode 32A functions as a working electrode, while the electrode 32B functions as a counter electrode. Hereinafter, the electrode 32A is referred to as the working electrode 32A, while the electrode 32B is termed as the counter electrode 32B as the case may be. Note that the example shown in FIG. 1 omits the illustration of a reference electrode, however, the reference electrode is formed by coating or printing silver-silver chloride over a predetermined area of the metal layer making up the counter electrode 32B.

The enzyme-immobilized layer 36 is formed by immobilizing, e.g., glucose dehydrogenase (GDH) defined as an enzyme reacting on the glucose onto the carbon layer by dint of glutaraldehyde defined as a crosslinker. Glucose oxidase (GOD) can be also applied as a substitute for the glucose dehydrogenase.

The other end portion 3B is formed with a circular through-hole 35 functioning as an attaching portion to the monitoring instrument 2 in a manner that is concentric with the circle which shapes the other end 3B. The through-hole 35 is formed so that the central line C1 passes through the center of the through-hole 35. Namely, the through-hole 35 is disposed on the central line C1 of the one end portion 3A.

The contact pads 33A, 33B are used for electrically connecting the electronic components within the monitoring instrument 2 to the working electrode 32A and the counter electrode 32B. In the example shown in FIG. 1, the contact pads 33A, 33B are formed each in a circular arc that is concentric with the circle shaping an inner periphery of the through-hole 35 as well as in bilateral symmetry with respect to the central line C1. It is not, however, an indispensable requirement that the contact pads are disposed in bilateral symmetry (line symmetry). Further, the contact pads 33A, 33B are disposed on the same imaginary circle. The contact pads 33A, 33B may, however, be disposed on different concentric imaginary circles, respectively. Moreover, the contact pads 33A, 33B may be disposed in any positions of the should-be-disposed imaginary circle(s) if in a non-intersected state (in an insulated state) of lead wire(s) connected to both or each of the contact pads 33A, 33B.

As illustrated in FIGS. 2 and 3, a cylindrical shaft (cylinder) 21 serving as an attached portion is erected in an attaching position of the glucose sensor 3 on the upper surface of the base plate 2a of the monitoring instrument 2. The glucose sensor 3 is attached to the monitoring instrument 2 in such a way that the through-hole 35 formed in the other end portion 3B, with its one surface being directed upward, receives insertion of the shaft 21 (the through-hole 35 is supported about the shaft 21). At this time, the one end portion 3A of the glucose sensor 3 is set in a state of extending outside the housing 2 via an insertion port 2c formed in the base plate 2a.

An outside diameter of the shaft 21 is formed substantially in the same size as an inside diameter of the through-hole 35. With this contrivance, the glucose sensor 3 attached to the monitoring instrument 2 comes to a state of being attached to the monitoring instrument 2 so that the through-hole 35 is coaxial with the shaft 21, thus reaching a state of being rotatable about the shaft 21. Shafts 22A, 22B functioning as stoppers are, however, erected from an upper surface of the base plate 2*a*, and the one end portion 3A of the glucose sensor 3, which extends from the other end portion 3B, stretches to the insertion port 2*c* via between the shafts 22A and 22B.

Accordingly, in FIG. 3, the shaft 22A regulates clockwise rotations of the glucose sensor 3, while the shaft 22B regulates counterclockwise rotations thereof. Thus, the glucose sensor 3 (the base plate 31) swings (rotates) relatively to the monitoring instrument 2 within a range between the shaft 22A and the shaft 22B.

Note that the shafts 22A, 22B are, as described above, the stoppers (regulating portions) provided for regulating the swing range of the glucose sensor 3 and may therefore be what abuts on the glucose sensor 3 to regulate the rotations (swings) thereof without limiting its shape to the shaft-like shape.

Another available scheme is that, for example in FIG. 3, the shafts 22A, 22B are omitted, and internal walls (indicated by 2*c*1, 2*c*2 in FIG. 3) of the base plate 2*a* that define the insertion port 2*c* receive the rotations of the glucose sensor 3, thus allowing the glucose sensor 3 to swing. In this case, the internal walls 2*c*1, 2*c*2 function as the stoppers (the regulating portions).

An swing angle of the glucose sensor 3 may be properly set. Further, in the example shown in FIG. 3, when the state where the central line C1 of the glucose sensor 3 extends in one direction (in a direction X in FIG. 3) on the flat surface of the base plate 2*a* of the monitoring instrument 2 is set as an initial state, ranges (angular ranges) in which the glucose sensor 3 may swing in the clockwise direction and counterclockwise direction from the initial position are substantially equal to each other. The swing ranges in both directions may also be differentiated.

Next, a connecting portion for establishing the electric connection between the monitoring instrument 2 and the glucose sensor 3 will be discussed. As illustrated in FIGS. 2 and 3, the interior of the housing for the monitoring instrument 2 is provided with contacts (terminals) 23*a*, 23*b* that are respectively brought into contact with the contact pads 33A, 33B of the glucose sensor 3 fitted to the shaft 21. Only the contact 23*b* of these contacts is illustrated in FIG. 2.

The terminals 23*a*, 23*b* are fitted in an insulating state to lower edges of compression springs 24, (an illustration of the compression spring 24 corresponding to the terminal 23*a* is, however, omitted in FIG. 2) provided respectively at the terminal 23*a* and the terminal 23*b*. An upper edge of the compression spring 24 is fitted in a fixed state to the undersurface of the substrate 6 in the example of FIG. 2. As a matter of course, the upper edge of the compression spring 24 may be fitted to a support member provided within the housing and may also be fitted in the fixed state to the surface of the internal wall of the housing.

The respective compression springs 24, 24 bias the terminals 23*a*, 23*b* downward, with the result that the individual terminals 23*a*, 23*b* are kept in contact with the corresponding contact pads 33A, 33B in a state of being pressed against the upper surfaces of the contact pads 33A, 33B. Each of the terminals 23*a*, 23*b* is connected to the electronic component provided on the substrate 6 via the unillustrated lead line(s). As a result, the working electrode 32A and the counter electrode 32B get electrically connected to the electronic components of the monitoring instrument 2. Note that the compression spring 24 may also be an elastic member such as a rubber member other than the spring.

The respective terminals 23*a*, 23*b* are, for instance, as shown in FIG. 3, orthogonal to the central line C1 extending in the direction X and are disposed on the straight line passing through the center of the shaft 21. Herein, the substrate 6 is fixedly disposed with the aid of an unillustrated support member within the housing. For example, an arrangement is that the substrate 6 is secured by screws to the base plate 2*a* or the cover 2*b*, and, if the base plate 2*a* and the cover 2*b* are joined in a predetermined position, the terminals 23*a*, 23*b* are disposed in positions shown in FIG. 3 with respect to the shaft 21.

As described above, the contact pads 33A, 33B are formed in the circular arcs each concentric with the through-hole 35 (the shaft 21). Accordingly, when the glucose sensor 3 swings about the shaft 21, it follows that the terminals 23*a*, 23*b* relatively move (slide) in a manner that depicts trajectories of the circular arcs on the corresponding contact pads 33A, 33B. In FIG. 3, the relatively-moving terminals 23*a*, 23*b* are depicted by broken lines. The circular arcs of the metal layers, which configure the contact pads 33A, 33B, are formed to have lengths enabling the respective terminals 23*a*, 23*b* to be constantly kept in a fixed abutting state with the contact pads 33A, 33B in the oscillation range of the glucose sensor 3.

Note that it may be sufficient to keep the preferable abutting state between the contact pads 33A, 33B and the terminals 23*a*, 23*b* in the swing range of the glucose sensor 3, and it is therefore feasible to apply, without any necessity that the contact pads 33A, 33B take the circular arcs in their outer edge shapes, a variety of shapes such as a circle, an elliptic, an oblong and a polygon each capable of embracing a movement range of the circular arcs of the terminals 23*a*, 23*b*. As a matter of course, the formation of the circular arcs enables the materials to be saved by minimizing areas of the contact pads 33A, 33B.

Moreover, the terminals 23*a*, 23*b* do not need disposing on the straight including the center of the shaft 21 but may be disposed so as to move on the circular arcs with the shaft 21 being centered in response to the swing of the glucose sensor 3, and the contact pads 33A, 33B are, it may be enough, formed corresponding thereto. Further, the shaft 21 is exemplified as the fixed shaft but may be constructed in a way that is supported by an unillustrated bearing and thus rotates integrally with the glucose sensor 3, corresponding to the swing of the glucose sensor 3.

As illustrated in FIG. 2, a bonding film 15 is bonded to the external surface of the base plate 2*a*. The bonding film 15 is used for fixedly bonding the monitoring instrument 2 onto a skin 16 of the examinee. The bonding film 15 involves using, e.g., a double-sided tape having adhesions on both faces. The sensor unit 4 is bonded onto the skin, in which case such a state occurs that the one end portion 3A, extending from the lower portion of the housing, of the glucose sensor 3 is embedded subcutaneously, and the sensor unit (the working electrode 32A and the counter electrode 323) provided at the one end portion 3A is indwelled in the living organism.

With this arrangement, the working electrode 32A and the counter electrode 32B come to a state of being immersed in the subcutaneous interstitial liquid. In this state, when a predetermined voltage is applied to between the working electrode 32A and the counter electrode 32B, an electric current flows upon the reaction between the GDH of the enzyme-immobilized layer 36 of the working electrode 32A and the glucose in the interstitial liquid, and it follows that the current is transmitted as a signal indicating the glucose in the interstitial liquid to the electronic components on the substrate 6 via the contact pads and the terminals.

Figure 4:
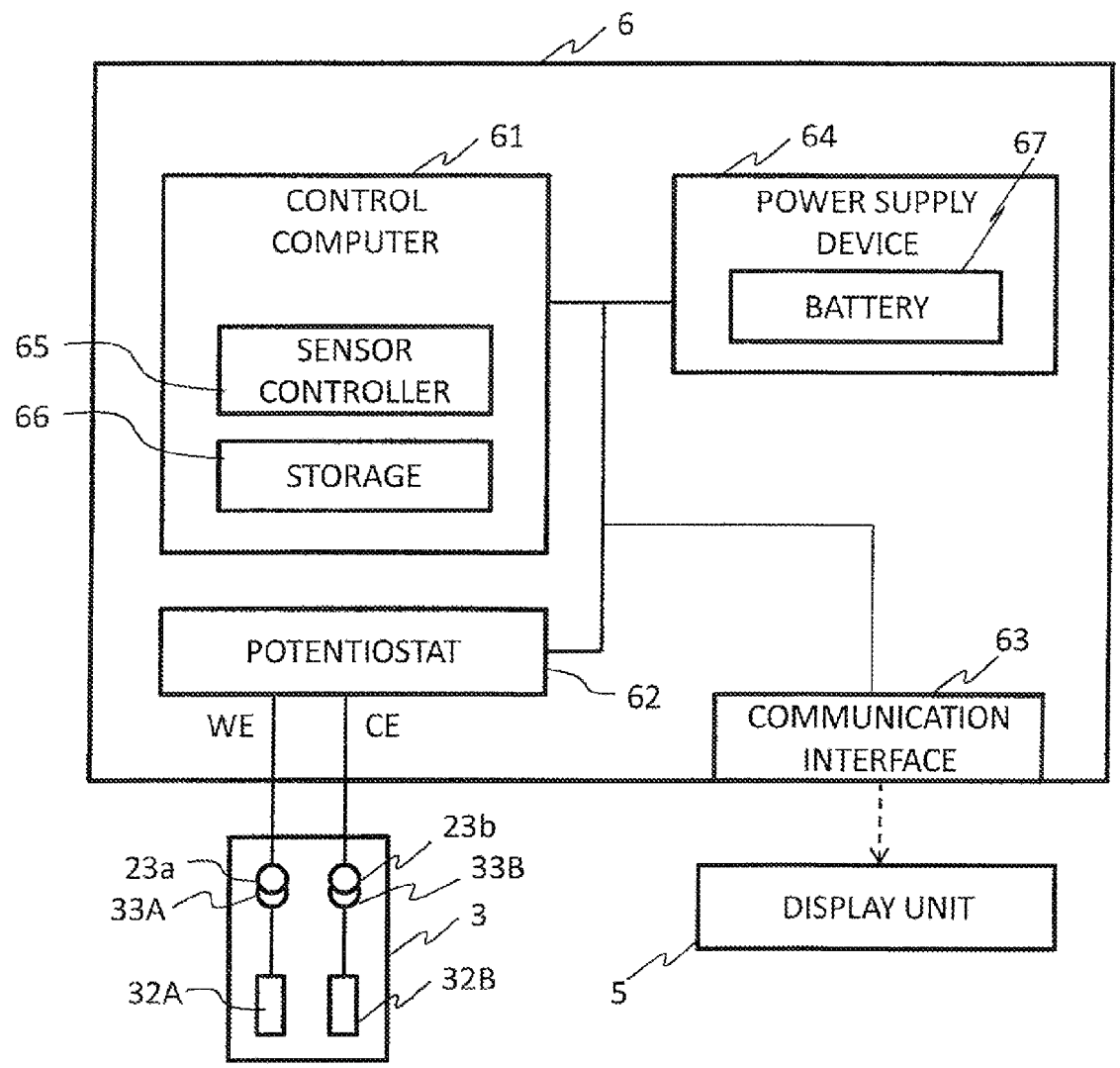
FIG. 4 is a block diagram schematically depicting a group of electronic components mounted on a substrate shown in FIG. 2.

FIG. 4 is a block diagram schematically showing the electronic components mounted on the substrate 6. The substrate 6 is packaged with the electronic components that compose a control computer 61, a potentiostat 62, a communication interface 63 and a power supply device 64, which are connected to each other.

The potentiostat 62 is a device which makes constant the electric potential of the working electrode 32A with respect to the reference electrode (unillustrated). The potentiostat 62 has a terminal WE for the working electrode and a terminal CE for the counter electrode, the terminal WE is connected to the terminal 23a via the lead line(s) (unillustrated), and the terminal 23a is brought into contact with the contact pad 33A, whereby the working electrode 32A is connected to the terminal WE. Similarly, the terminal CE is connected to the terminal 23b via the lead line(s) (unillustrated), and the terminal 23b is brought into contact with the contact pad 33B, whereby the counter electrode 32B is connected to the terminal CE.

The potentiostat 62 applies a predetermined voltage to between the counter electrode 32B and the working electrode 32A via the terminals WE, CE, then measures a response current of the working electrode 32A that is acquired at the terminal WE, and transmits a monitored result of the response current to the control computer 61.

The control computer 61 includes hardwarewise a processor such as a CPU (Central Processing Unit), a recording medium such as a memory (RAM (Random Access Memory)) and a ROM (Read Only Memory) and an unillustrated Input/Output (I/O) device. The computer 61 functions as a device including a controller 65 and a storage 66 in such a manner that the processor loads the program stored on the recording medium (e.g., the ROM) into the RAM and then executes the program. Note that the control computer 61 may also include an auxiliary storage device such as a semiconductor memory (EEPROM (Electrically Erasable Programmable ROM, a flash memory) and a hard disc.

The controller 65 controls a voltage application timing, an applied voltage value, sampling of the response current, the computation of the glucose concentration or communications with external information processing terminal (the display unit 5). On the occasion of executing the control, the processor (CPU) uses data prepared beforehand on the storage 66 and data temporarily stored in the working area provided on the storage 66.

The communication interface 63 performs data communications with the display unit 5, and transmits the computed result of the glucose concentration given by the controller 65 to the display unit 5. Communications available as the data communications are wired communications using a cable, and noncontact (wireless) communications (e.g., IrDA, Bluetooth) utilizing infrared-rays and radio transmission can be also applied.

The display unit 5 includes a communication interface performing the communications with the monitoring instrument 2, a display panel (a display device) and a control device for the display device. In the display unit 5, the communication interface receives the computed result of the glucose concentration transmitted from the monitoring instrument 2, and the control device displays the computed result in a predetermined format on the display screen of the display device. The display unit 5 may be, similarly to the monitoring instrument 2, disposed in the way of being bonded onto the skin 16 of the examinee by providing the bonding film on the undersurface of the display unit 5. Alternatively, the display unit 5 may be also disposed in a predetermined position excluding the on-the-skin area in the communication-enabled range with the monitoring instrument 2.

The power supply device 64, which has a battery 67, supplies the electric power for operation to the respective components of the electronic components such as the control computer 61, the potentiostat 62 and the communication interface 63. Note that the power supply device 64 may be also mounted outside the housing for the monitoring instrument 2.

Incidentally, an available scheme is that the display unit 5 incorporates the functions as the controller 65 and the storage unit 66 of the control computer 61 and, on the side of the monitoring instrument 2, the communication unit 63 transmits the monitored result of the response current by the potentiostat 62 to the display unit 5. Alternatively, another available scheme is that the display unit 5 is mounted with the control computer 61 and the potentiostat 62, in which the potentiostat 62 mounted on the display unit 5 executes applying the voltage to the glucose sensor 3 and detecting the response current.

Next, an operational example of the monitoring apparatus 1 described above will be discussed. In the case of continuously monitoring the glucose concentration of the examinee, the sensor units (the monitoring instrument 2 and the glucose sensor 3) are properly set in predetermined locations (an abdomen region or an arm region) of the examinee, and the one end portion 3A of the glucose sensor 3 is subcutaneously indwelled, and the electrodes 32A, 32B are immersed in the interstitial liquid.

Thereafter, a start instruction of monitoring the glucose concentration, which is issued from the outside, is inputted to the controller 65 of the control computer 61. Herein, the monitoring instrument 2 includes an unillustrated input device, and the controller 65 starts and finishes, based on a monitoring start instruction and a monitoring end instruction each inputted via this input device, monitoring the glucose concentration or the response current.

The controller 65 accepting the monitoring start instruction starts applying the predetermined voltage to between the counter electrode 32B and the working electrode 32A by controlling the potentiostat 62 and also starts monitoring the response current given from the working electrode 32A. The potentiostat 62 monitors each response current obtained by applying the voltage and transmits the monitored response current to the controller 65.

The controller 65 executes, based on the response current value (a current density per unit time (t)), the process of computing the glucose concentration by employing a known technique (algorithm), thus computing the glucose concentration for the time (t). For example, the storage 66 previously retains calibration curve data of the glucose concentration corresponding to the GDH in the enzyme-immobilized layer 36 formed on the working electrode 32A, and the controller 65 computes the glucose concentration by use of the calibration curve indicated by the calibration curve data. Alternatively, the controller 65 computes the glucose concentration by substituting the response current value into a predetermined arithmetic formula for the glucose concentration. The controller 65 sends the computed result of the glucose concentration to the communication interface 63.

The communication interface 63 transmits the computed result of the glucose concentration, which is received from the controller 65, to the display unit 5. Thereafter, the controller 65 continuously executes, till the monitoring end instruction is inputted, the process of monitoring the response current value and computing the glucose concentration, and transmits the results to the display unit 5. The display unit 5 consecutively receives the computed results (the monitored results) of the glucose concentration from the monitoring instrument 2, whereby, e.g., the control device creates a graph by plotting time-based variations in glucose concentration and displays the graph on the display screen of the display device.

According to the first embodiment, if the examinee moves or some force is applied from outside to the housing for the monitoring instrument 2 during the monitoring of the response current in the operational example described above, it might happen that the external force is applied to the one end portion 3A of the subcutaneously-embedded glucose sensor 3. At this time, the glucose sensor 3 is attached to the monitoring instrument 2 in the way of being enabled to swing about the shaft 21 and therefore swings (rotates) relatively to the monitoring instrument 2, whereby the external force may be absorbed. This absorption prevents tissues of the examinee in the periphery of the one end portion 3A from being damaged.

Further, in the first embodiment, the contact pads 33A, 33B are provided over the range in which the terminals 23a, 23b move relatively to the swing of the glucose sensor 3, and it is therefore feasible to maintain a satisfactory state of the electric connections between the electrodes 32A, 32B and the monitoring instrument 2 even when the glucose sensor 3 swings.

The first embodiment can be modified as follows. To be specific, the outer periphery of the base plate 31 (FIG. 1) of the glucose sensor 3 in the first embodiment takes such a shape that one end (the intermediate portion and the one end portion 3A) of the rectangle is joined to the other circular end (the other end portion 3B). Namely, the whole outer edge of the other end of the base plate 31 is formed by the curves (e.g., circular arcs). By contrast, the outer edge shape of another end includes the portion of the straight lines, i.e., the outer edge of another end may be shaped by the curves and the straight lines. Further, the entire outer edge of the glucose sensor 3 may also be shaped by a triangle and a polygon.

Figure 5:
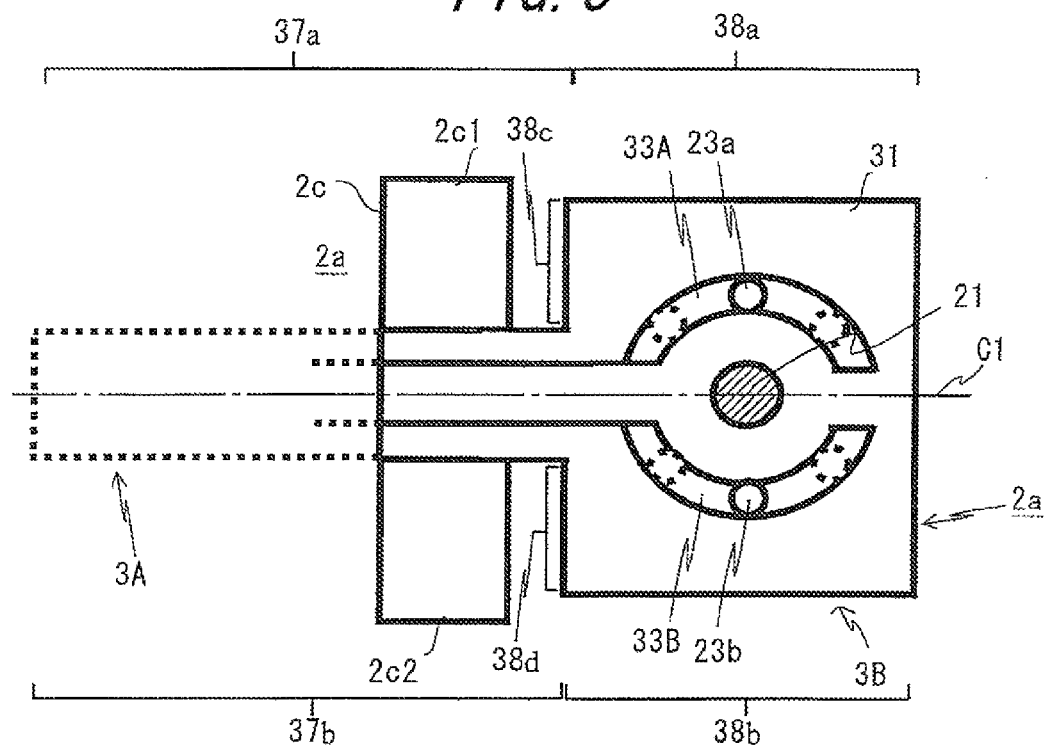
FIG. 5 is a view showing a modified example of the first embodiment.
Figure 6:
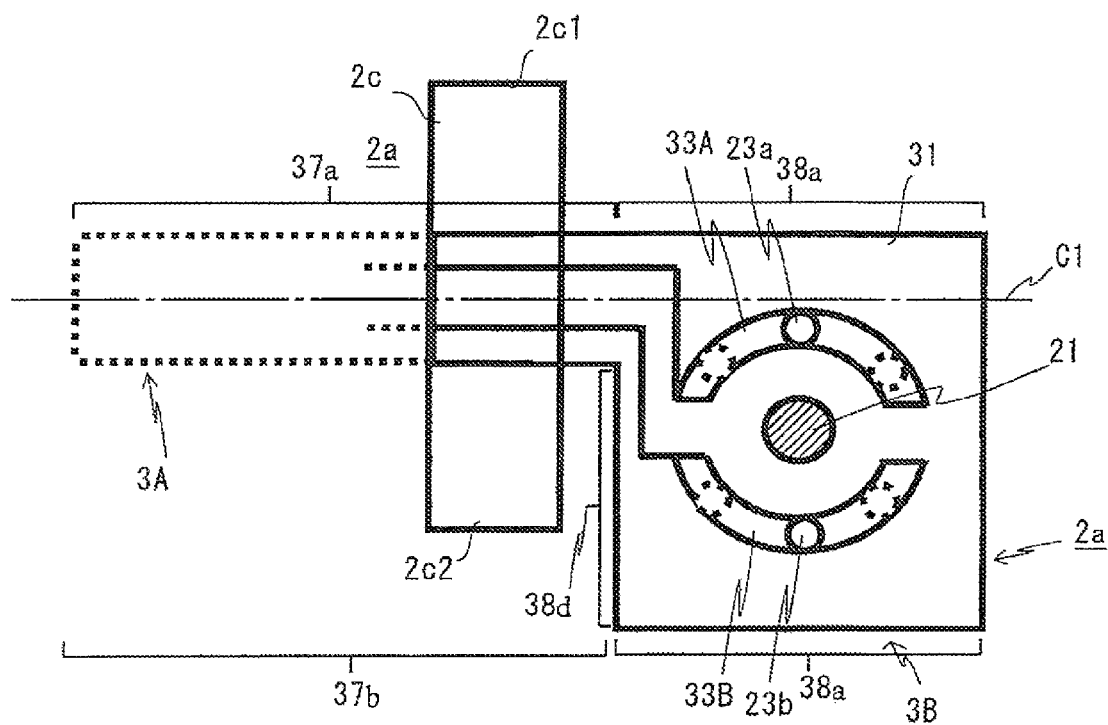
FIG. 6 is a view showing a modified example of the first embodiment.

FIGS. 5 and 6 are views showing modified examples of the first embodiment. FIG. 5 is a plan view schematically depicting the state of attaching a glucose sensor 3a according to the modified example to the monitoring instrument 2 described above. In FIG. 5, the glucose sensor 3a is different from the glucose sensor 3 (FIG. 1) in terms of such a point that the outer periphery of the other end portion 3B takes a rectangle.

Specifically, the shape of the outer periphery of the glucose sensor 3a illustrated in FIG. 5 may be explained as below. Namely, in a state of viewing the base plate 31 in plane, the intermediate portion and the one end portion 3A of the base plate 31, respectively extend in the longitudinal direction (in the direction of the central line C1 or the direction along the central line C1) of the glucose sensor 3a and include a first side 37a and a second side 37b in a face-to-face relation. By contrast, the other end portion 3B of the base plate 31 extends in the longitudinal direction of the glucose sensor 3a and includes a third side 38a and a fourth side 38b in the face-to-face relation. The first side 37a and the third side 38a are joined in a way that interposes another side 38c in a direction intersecting the longitudinal direction. On the other hand, the second side 37a and the fourth side 38b are joined in a manner that interposes another side 38d in a direction intersecting the longitudinal direction.

Note that another side 38c and still another side 38d are disposed in the directions orthogonal to the longitudinal direction (the direction of the central line C1) in the example of FIG. 5. As a matter of course, these sides may be disposed in directions intersecting the longitudinal direction at angles excluding the right angle. Alternatively, the sides 38c, 38d may be formed by the curves.

Moreover, a scheme in the modified example illustrated in FIG. 5 is that the central line C1 (the central line of one end portion) of the glucose sensor 3a passes through the center of the shaft 21, and the glucose sensor 3a is constructed in bilateral symmetry with respect to the central line C1. On the other hand, the monitoring instrument 2 does not include the shafts 22A, 22B (FIG. 3) for regulating the oscillations of the glucose sensor 3a, in which the oscillations of the glucose sensor 3a are regulated by the internal walls 2c1, 2c2 of the insertion port 2c. Other configurations and other operational effects are substantially the same as those of the glucose sensor 3 depicted in FIG. 1.

A glucose sensor 3b according to another modified example illustrated in FIG. 6 is constructed similarly to the glucose sensor 3a so that the other end portion 3B takes the rectangle. The glucose sensor 3b is, however, different from the glucose sensor 3a in terms of including the first side 37a and the third side 38a, which are directly connected to each other without interposing another side, and embracing an outer edge shape of the straight line portion where the first side 37a and the third side 38a are connected. Further, the glucose sensor 3b is set in a state where a central line C2 of one end portion does not pass through the center of the shaft 21. Note that in the example of FIG. 6 also, the monitoring instrument 2 is not equipped with the shafts 22A, 22B similarly to the example of FIG. 5, in which the oscillations of the glucose sensor 3b are regulated by the internal walls 2c1, 2c2. As shown in the example of FIG. 6, neither the passage of the central line of one end portion through the center of the shaft 21 nor the bilateral symmetry of the outer edge shape of the glucose sensor is an essential requirement for the construction.

Incidentally, as stated above, the outer periphery of the other end portion may take a shape of the straight line and the curve, and, for example, in the glucose sensors 3a and 3b shown in FIGS. 5 and 6, at least one of the sides shaping the outer periphery of the other end portion may be formed of the curve.

Second Embodiment

Next, a second embodiment of the present invention will be discussed. The second embodiment embraces the points that are common to the first embodiment, and therefore the discussion will focus on different points in a way that omits the descriptions of the common points. Further, in the configurations of the glucose sensor and the monitoring instrument according to the second embodiment, the same components as those in the first embodiment are marked with the same numerals and symbols.

Figure 7:
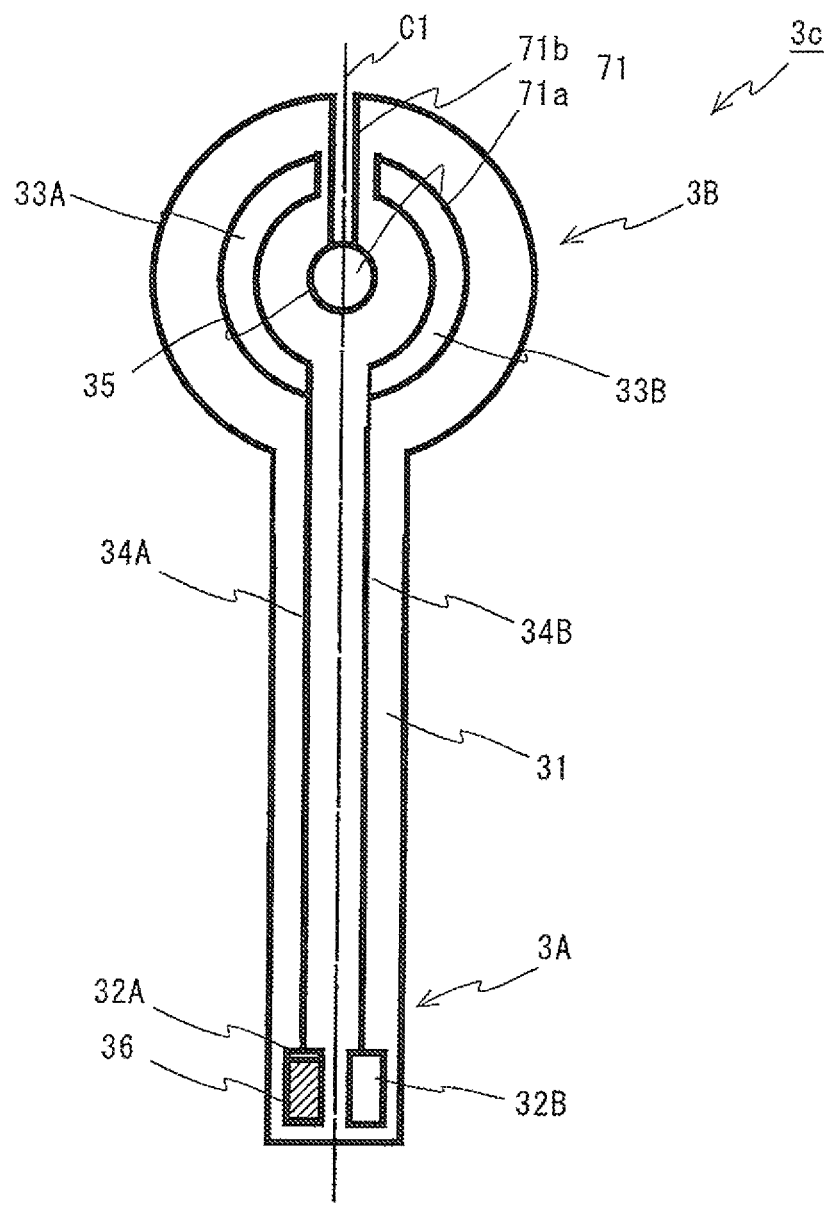
FIG. 7 is a view showing an example of a configuration of the electrochemical sensor (glucose sensor) according to a second embodiment.
Figure 8:
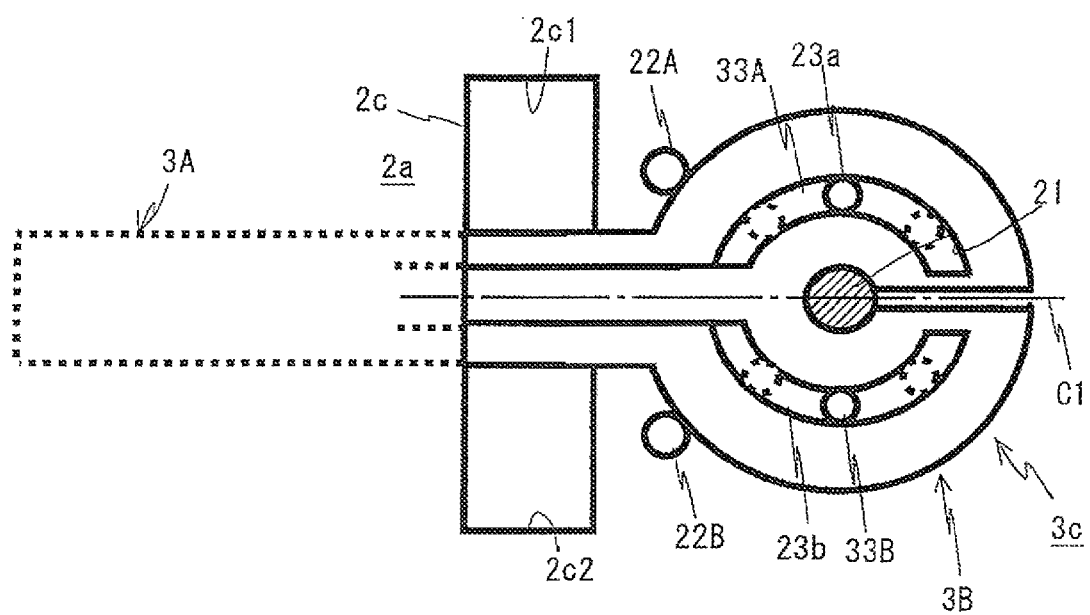
FIG. 8 is a view showing a state where the glucose sensor attached to the monitoring instrument according to the second embodiment is viewed in plane from above.

FIG. 7 is a view illustrating an example of a configuration of an electrochemical sensor (a glucose sensor 3c) according to the second embodiment. FIG. 8 schematically illustrates a state in which the glucose sensor 3c attached to the monitoring instrument is viewed in plane from above.

As illustrated in FIG. 7, the glucose sensor 3c according to the second embodiment is different from the glucose sensor 3 according to the first embodiment in terms of having a notched portion 71 as a substitute for the through-hole 35 formed in the glucose sensor 3 (FIG. 1). The notched portion 71 includes a first portion 71a taking a circular shape and a second portion 71b having a rectilinear shape, which is formed so as to connect the first portion 71a to the outer periphery of the other end portion 3B.

The first portion 71a corresponds to the through-hole 35 in the first embodiment has its inside diameter formed in the way of matching with the outside diameter of the shaft 21, and an inner periphery of the first portion 71a is formed concentrically with the shaft 21. In contrast with this, a width of the second portion 71b is set smaller than the outside diameter of the shaft 21. Except the points described above, the glucose sensor 3c according to the second embodiment has the same configuration as the glucose sensor 3 in the first embodiment has. The glucose sensor 3c can be applied to the monitoring instrument 2 and the display unit 4 explained in the first embodiment and is capable of continuously monitoring the glucose as described in the first embodiment.

According to the second embodiment, the glucose sensor 3c includes the notched portion 71. On the occasion of attaching the glucose sensor 3c to the monitoring instrument 2, the glucose sensor 3c is intruded so that the shaft 21 is inserted into the second portion 71b of the notched portion 71, and the shaft 21 is fitted into the first portion 71a, whereby the glucose sensor 3c comes to the state of being attached to the monitoring instrument 2. This arrangement facilitates the attaching operation as compared with the case of getting the shaft 21 inserted into the through-hole 35 in the first embodiment.

Note that a width of the second portion 71b may set equal to or smaller than a radius of the shaft 21, thereby making it possible to prevent the shaft 21 from being easily removed from the first portion 71a. Moreover, the examples of FIGS. 7 and 8 have shown that the second portion 71b is provided in the longitudinal direction (the direction of the central line C1) of the glucose sensor 3c, however, the second portion may be provided in the direction intersecting (e.g., in the direction orthogonal to) the longitudinal direction. In this case, it is feasible to prevent the glucose sensor 3c attached to the shaft 21 from coming off the shaft 21 in a manner that resists tensile force acting in the longitudinal direction.

Third Embodiment

Next, a third embodiment of the present invention will be discussed. The third embodiment embraces the points that are common to the first embodiment, and therefore the discussion will focus on different points in a way that omits the descriptions of the common points. Further, in the configurations of the glucose sensor and the monitoring instrument according to the third embodiment, the same components as those in the first embodiment are marked with the same numerals and symbols.

Figure 9:
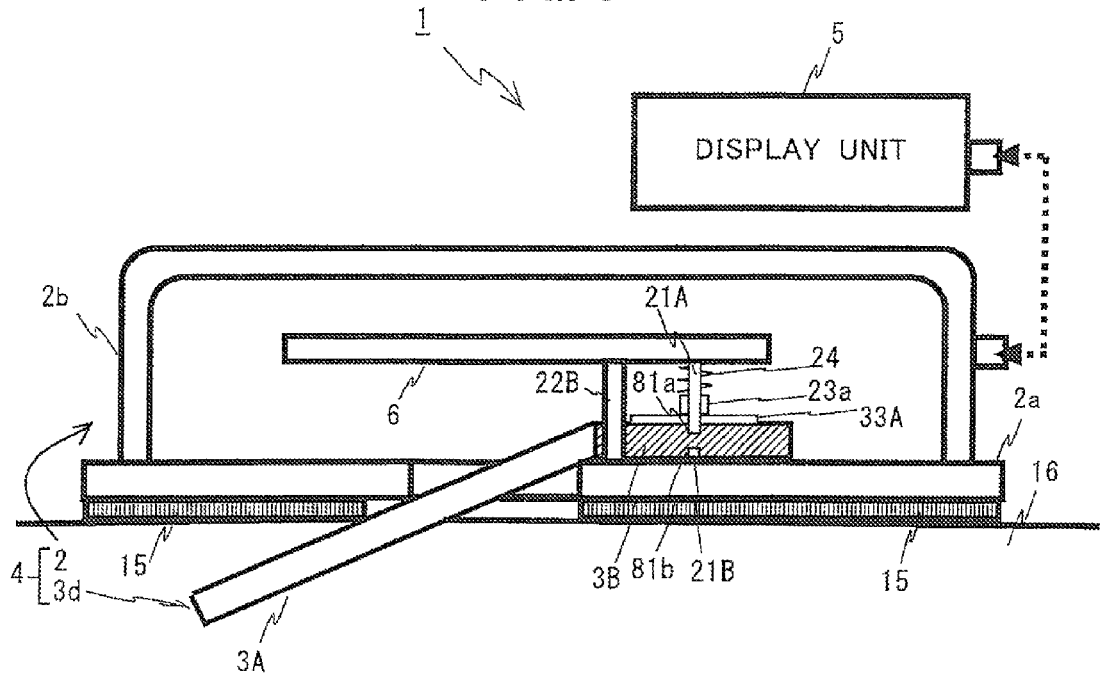
FIG. 9 is a view schematically showing a state where the electrochemical sensor (glucose sensor) according to a third embodiment is attached to the monitoring instrument.
Figure 10:
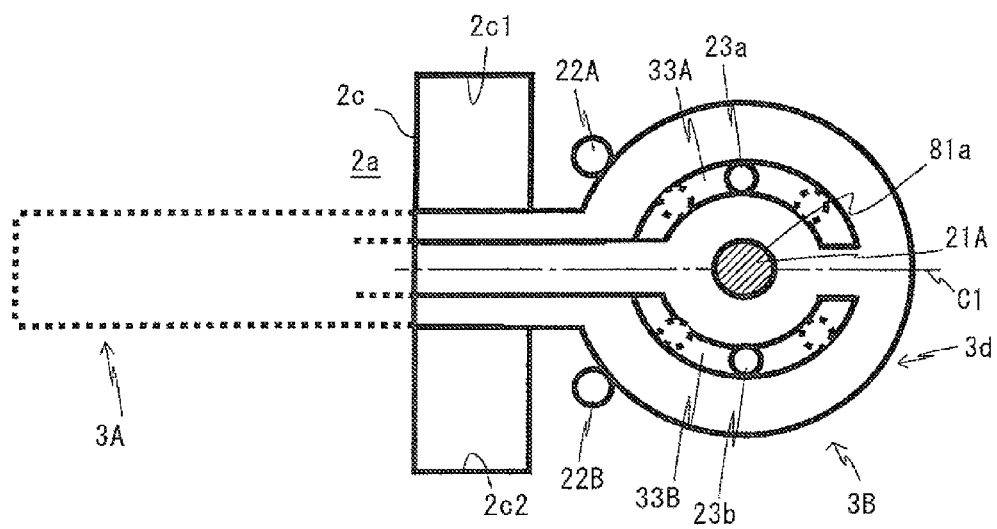
FIG. 10 is a view schematically showing a state where the glucose sensor attached to the monitoring instrument according to the third embodiment is viewed in plane from above.

FIG. 9 schematically illustrates a state in which the electrochemical sensor (a glucose sensor 3d) according to the third embodiment is attached to the monitoring instrument 2. FIG. 10 schematically, shows a state where the glucose sensor 3d attached to the monitoring instrument 2 is viewed in plane from above.

As depicted in FIGS. 9 and 10, the glucose sensor 3d according to the third embodiment has a recessed portion 81a and a recessed portion 81b in place of the through-hole 35 formed in the glucose sensor 3 according to the first embodiment.

At the other end portion 3B of the glucose sensor 3d, the recessed portion 81a is formed in a surface (which is referred to as an electrode forming surface) formed with the contact pads 33A, 33B (the electrodes 32A, 32B (unillustrated)) of the base plate 31, and the recessed portion 81b is formed in a reversed surface of the electrode forming surface concentrically with the recessed portion 81a. Each of the recessed portions 81a, 81b is formed in circle concentric with the circle which shapes the outer periphery of the other end portion 3B of the glucose sensor 3d, and the central line C1 of the glucose sensor 3d passes through the center of each of the recessed portions 81a, 81b.

On the other hand, as illustrated in FIG. 9, the interior of the housing for the monitoring instrument 2 is provided with shafts (protruded portions) 21A, 21B in place of the shaft 21 in the first embodiment. The shaft 21B is erected in the attaching position of the glucose sensor 3d on the upper surface of the base plate 2a, and the other end portion 3B of the glucose sensor 3d is mounted in the attaching position in the state of getting the shaft 21B inserted into the recessed portion 81b. An arrangement is that one end of the shaft 21A is supported in the way of being secured to, e.g., the undersurface of the substrate 6, and, when the base plate 2a and the cover 2b are properly joined together, the other end of the shaft 21A is inserted into the recessed portion 81a. Note that one end of the shaft 21A may also be supported in the way of being secured to an internal surface of the cover 2b.

Thus, according to the third embodiment, the recessed portions 81a and 81b function as bearings for the shafts 21A and 21B, and the shafts 21A, 21B are coaxially inserted into the recessed portions 81a, 81b. Namely, when attaching the glucose sensor 3d, the respective ends of the two shafts 21A, 21B included by the monitoring instrument 2 and disposed in the face-to-face state on the same straight line are inserted into the recessed portions 81a, 81b. With this arrangement, the glucose sensor 3d gets enabled to oscillate in the direction of the plane of the sensor.

Except the constructive arrangement described above, the configurations of the glucose sensor 3d, the monitoring instrument 2 and the display unit 5 are the same as those in the first embodiment, and hence their descriptions are omitted. The third embodiment may acquire substantially the same operational effects as those in the first embodiment.

Fourth Embodiment

Next, a fourth embodiment of the present invention will be discussed. The fourth embodiment embraces the points that are common to the first embodiment. Therefore, the discussion will focus on different points in a way that omits the descriptions of the common points. Further, in the configurations of the glucose sensor and the monitoring instrument according to the fourth embodiment, the same components as those in the first embodiment are marked with the same numerals and symbols.

Figure 11:
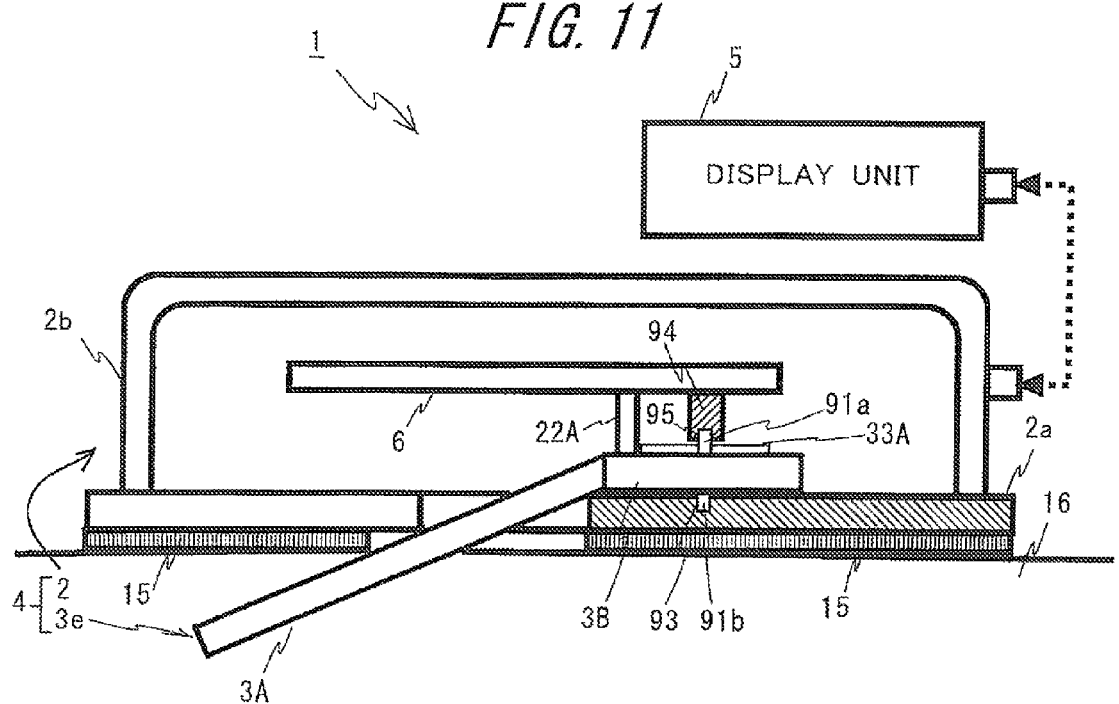
FIG. 11 is a view schematically showing a state where the glucose sensor attached to the monitoring instrument according to a fourth embodiment is viewed in plane from above.
Figure 12:
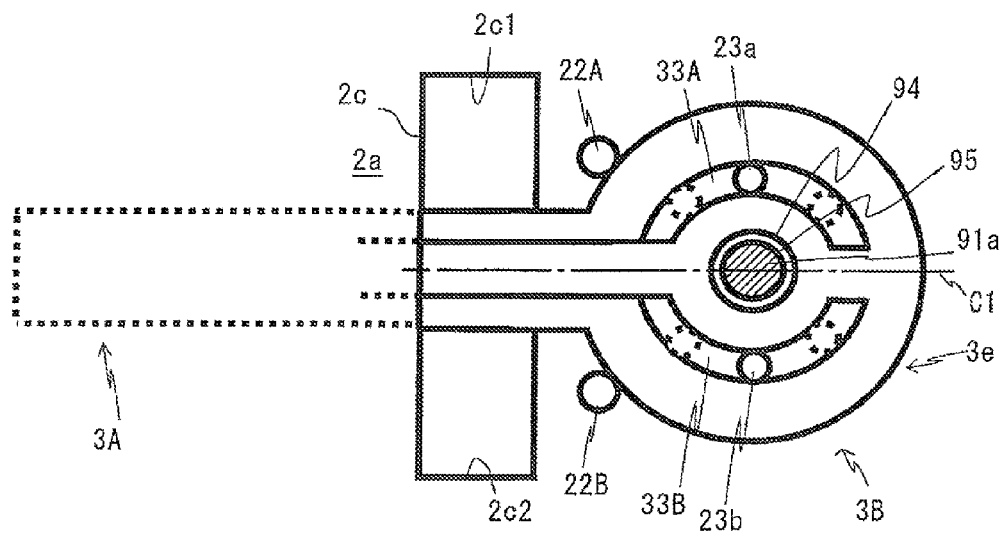
FIG. 12 is a view schematically showing a state where the glucose sensor attached to the monitoring instrument according to a fourth embodiment is viewed in plane from above.

FIG. 11 schematically illustrates a state in which the electrochemical sensor (a glucose sensor 3e) according to the fourth embodiment is attached to the monitoring instrument 2. FIG. 12 schematically shows a state where the glucose sensor 3e attached to the monitoring instrument 2 is viewed in plane.

As depicted in FIGS. 11 and 12, the glucose sensor 3e according to the fourth embodiment includes a protruded portion 91a and a protruded portion 91b in place of the through-hole 35 formed in the glucose sensor 3 according to the first embodiment. In FIG. 11, the illustrations of the terminal 23a (23b) and the compression spring 24 are omitted.

At the other end portion 3B of the glucose sensor 3e, the protruded portion 91a is formed on the electrode forming surface formed with the contact pads 33A, 33B (the electrodes 32A, 32B (unillustrated)) of the base plate 31. The protruded portion 91b is formed, coaxially with the protruded portion 91a, on the reversed surface of the electrode forming surface. Each of the protruded portions 91a, 91b is formed in a cylindrical shape concentric with the circle which shapes the outer periphery of the other end portion 3B of the glucose sensor 3e, and the central line C1 of the glucose sensor 3e passes through the center of each of the protruded portions 91a, 91b.

On the other hand, as depicted in FIG. 11, the interior of the housing for the monitoring instrument 2 is provided with a recessed portion 93 and a bearing portion 94 instead of the shaft 21 in the first embodiment. The recessed portion 93 is formed in the attaching position of the glucose sensor 3e on the upper surface of the base plate 2a, and the other end portion 3B of the glucose sensor 3e is mounted in the attaching position in a state where the protruded portion 91b is inserted into the recessed portion 93. The recessed portion 93 functions as a bearing for the protruded portion 91b.

While on the other hand, one end portion of the bearing portion 94 is fitted on, for example, an undersurface of the substrate 6 to be supported. When the base plate 2a and the cover 2b are properly joined together, the protruded portion 91a is inserted into the recessed portion 95 formed in the other end portion of the bearing portion 94. Thus, the recessed portion 95 functions as a bearing for the protruded portion 91a. Note that the one end portion of the bearing portion 94 may be fitted on the internal surface of the cover 2b to secure it.

Thus, in the fourth embodiment, in the state of attaching the glucose sensor 3e to the monitoring instrument 2, the protruded portions 91a, 91b provided on the glucose sensor 3e are inserted into the recessed portions 93, 95 formed in the monitoring instrument 2. To be specific, the glucose sensor 3e includes the two protruded portions 91a, 91b that are formed coaxially on the electrode forming surface and the reversed surface of the base plate 31. The protruded portions 91a, 91b are inserted into the two recessed portions 93, 95 formed in the monitoring instrument 2. Then, the protruded portions 91a, 91b and the recessed portions 93, 95 come to the state of being disposed coaxially, whereby the glucose sensor 3e gets enabled to swing in the direction of the plane of the sensor.

Except the configurations described above, the configurations of the glucose sensor 3e, the monitoring instrument 2 and the display unit 5 are the same as those in the first embodiment, and hence their descriptions are omitted. The fourth embodiment can acquire substantially the same operational effects as those in the first embodiment.

It should be noted that the configurations of the recessed portion 81b and the shaft 21B in the third embodiment may be replaced with the configurations of the protruded portion 91b and the recessed portion 93 in the fourth embodiment. Further, the configurations of the protruded portion 91a and the bearing portion 94 (the recessed portion 95) in the fourth embodiment can be replaced with the configurations of the recessed portion 81a and the shaft 21A in the third embodiment. Namely, it is feasible to build up the glucose sensor (the electrochemical sensor), in which the protruded portion can be provided on one of the electrode forming surface and the reversed surface, while the recessed portion is formed in the other surface.

Fifth Embodiment

Next, a fifth embodiment of the present invention will be discussed. The fifth embodiment embraces the points that are common to the first embodiment, and hence the discussion will focus on different points in a way that omits the descriptions of the common points. Further, in the configurations of the glucose sensor and the monitoring instrument according to the fifth embodiment, the same components as those in the first embodiment are marked with the same numerals and symbols.

Figure 13:
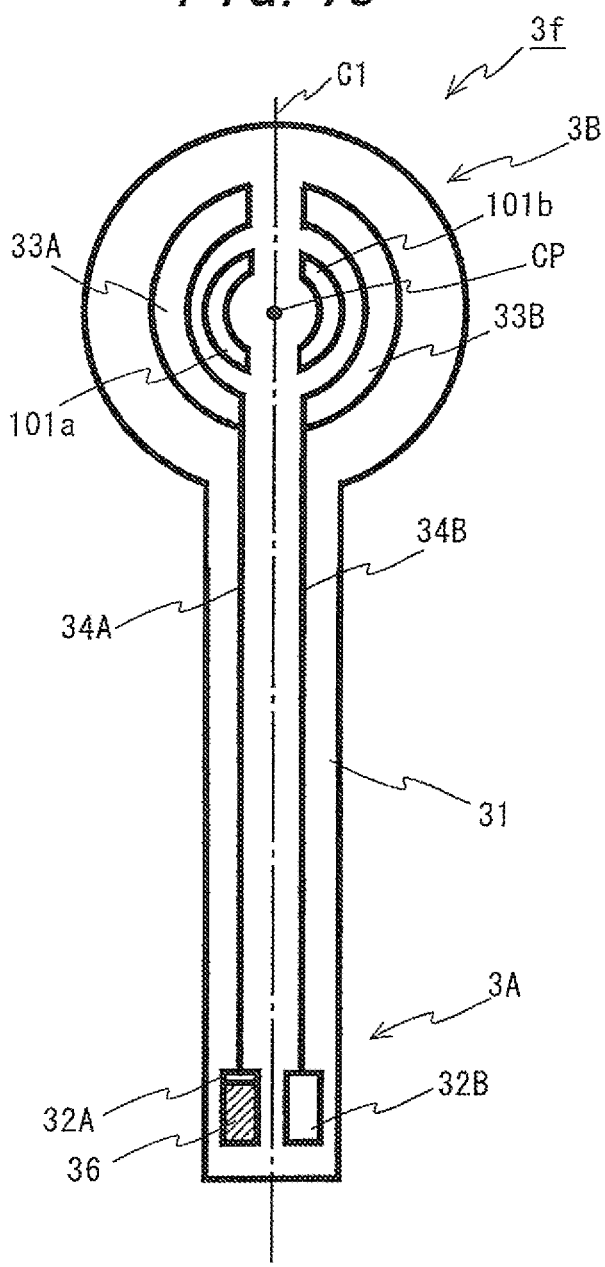
FIG. 13 is a view showing an example of a configuration of the electrochemical sensor (glucose sensor) according to a fifth embodiment.
Figure 14:
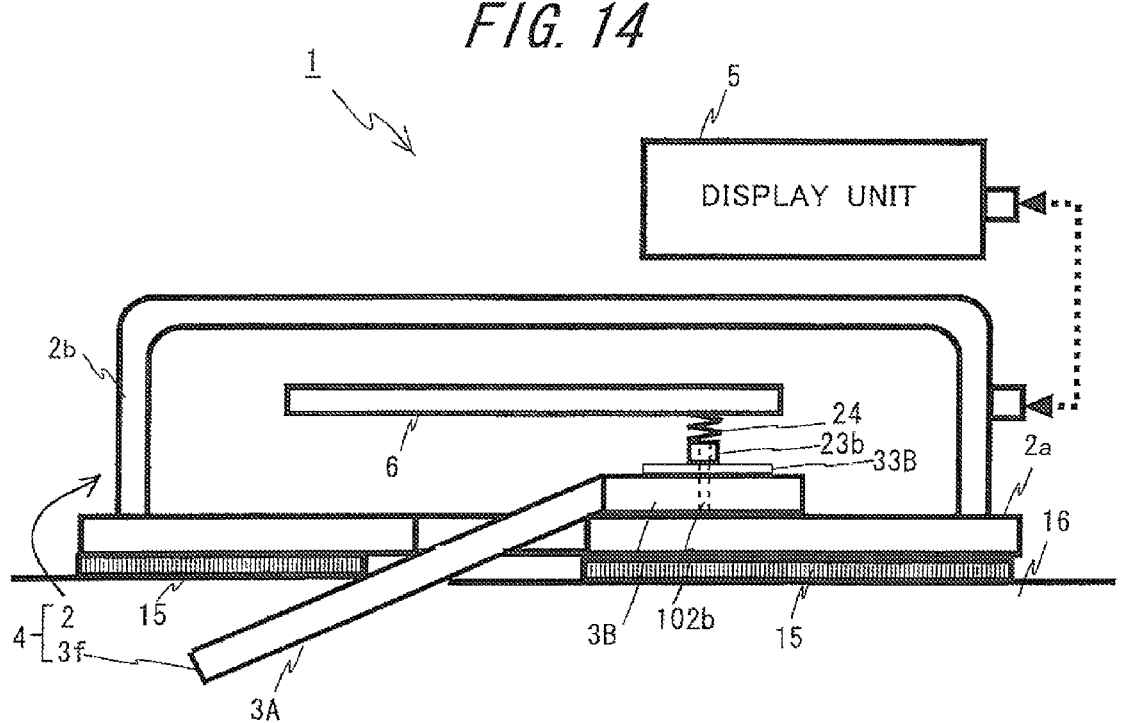
FIG. 14 is a view schematically showing a state where the electrochemical sensor (glucose sensor) according to the fifth embodiment is attached to the monitoring instrument.
Figure 15:
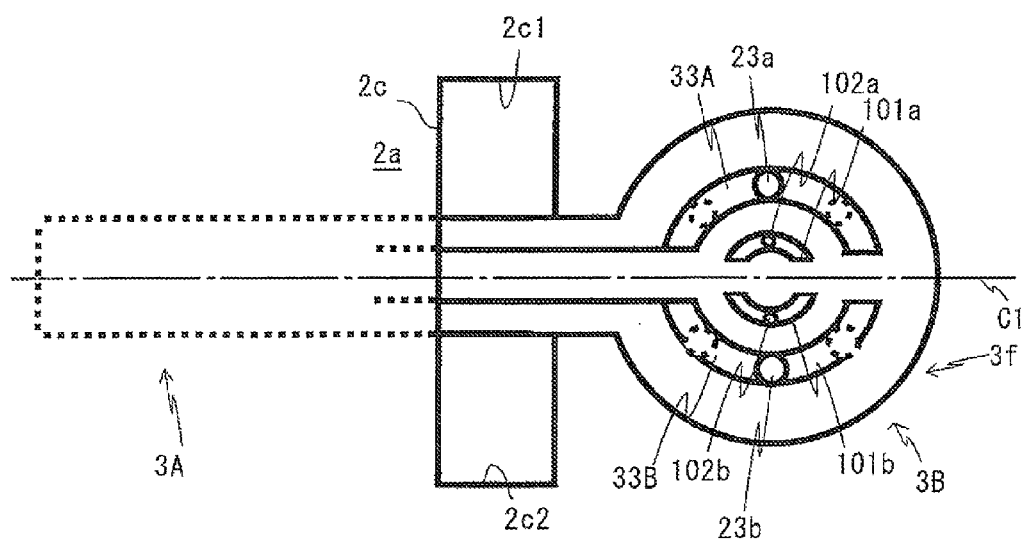
FIG. 15 is a view schematically showing a state where the glucose sensor attached to the monitoring instrument according to the fifth embodiment is viewed in plane from above.

FIG. 13 is a view illustrating an example of a configuration of the electrochemical sensor (a glucose sensor 3f) according to the fifth embodiment. FIG. 14 schematically illustrates a state in which the electrochemical sensor (the glucose sensor 3f) according to the fifth embodiment is attached to the monitoring instrument 2. FIG. 15 schematically shows a state where the glucose sensor 3f attached to the monitoring instrument 2 is viewed in plane from above.

As depicted in FIGS. 13 and 15, the glucose sensor 3f according to the fifth embodiment includes through-holes 101a, 101b serving as attaching portions in place of the through-hole 35 formed in the glucose sensor 3 according to the first embodiment.

In the example shown in FIG. 13, the through-holes 101a, 101b, which are concentric with respect to a center CP of the circular arcs formed by the contact pads 33A, 33B, are formed inwardly of the contact pads 33A, 33B. The through-holes 101a, 101b are disposed in line symmetry with respect to the central line C1 passing through the center CP of the circular arcs. It is not, however, an essential requirement that the through-holes 101a, 101b are disposed in line symmetry. Further, it is feasible to properly set which diameter of the circle that is concentric with respect to the center CP the through-holes 101a, 101b show the line symmetry with respect to. Moreover, it is sufficient that the through-holes 101a, 101b are concentric with respect to each other, and curvature radii thereof may be different from each other. Further, at least one of the through-holes 101a, 101b may be formed outwardly of the contact pads 33A, 33B.

On the other hand, as illustrated in FIGS. 14 and 15, two shafts 102a, 102b (only the shaft 102b is depicted in FIG. 14) instead of the shaft 21 in the first embodiment is provided within the housing for the monitoring instrument 2. The shafts 102a, 102b are erected in the attaching position of the glucose sensor 3f on the upper surface of the base plate 2a. The other end portion 3B of the glucose sensor 3f is mounted in the attaching position in a state where the shaft 102a gets inserted into the through-hole 101a, while the shaft 102b gets inserted into the through-hole 101b.

Thus, according to the fifth embodiment, in the position of attaching the glucose sensor 3f to the monitoring instrument 2, the shafts 102a, 102b provided on the monitoring instrument 2 come to the state of being inserted into the through-holes 101a, 101b formed in the glucose sensor 3f. Therefore, the glucose sensor 3f may swing in the direction of the plane of the sensor.

When the glucose sensor 3f swings clockwise, the swing thereof is controlled by the shafts 102a, 102b moving within the through-holes 101a, 101b, in which the shaft 102a contacts with the edge of the through-hole 101a on the side of the one end portion 3A, and/or the shaft 102b contacts with the edge of the through-hole 101b on the side of the other end portion 3B. Thus, the glucose sensor 3f stops clockwise swing. By contrast, when the glucose sensor 3f swings counterclockwise, the shaft 102b contacts with the edge of the through-hole 101a on the side of the one end portion 3A, and/or the shaft 102a contacts with the edge of the through-hole 101a on the side of the other end portion 3B, thereby the swing is stopped. Accordingly, in the fifth embodiment, the shafts 22A, 22B serving as the stoppers is omitted.

Except the constructive arrangement described above, the configurations of the glucose sensor 3f, the monitoring instrument 2 and the display unit 5 are the same as those in the first embodiment, and hence their descriptions are omitted. The fifth embodiment can acquire substantially the same operational effects as those in the first embodiment.

Sixth Embodiment

Next, a sixth embodiment of the present invention will be discussed. The sixth embodiment embraces the points that are common to the first embodiment, and hence the discussion will focus on different points in a way that omits the descriptions of the common points. Further, in the configurations of the glucose sensor and the monitoring instrument according to the sixth embodiment, the same components as those in the first embodiment are marked with the same numerals and symbols.

Figure 16:
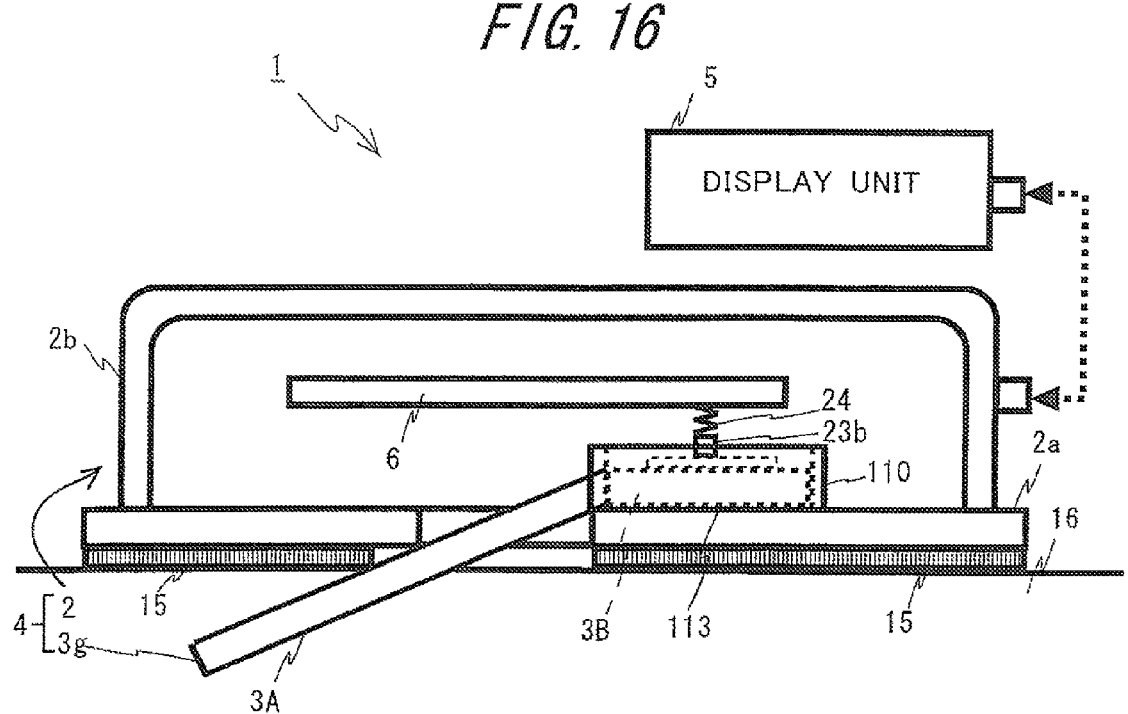
FIG. 16 is a view schematically showing a state where the electrochemical sensor (glucose sensor) according to a sixth embodiment is attached to the monitoring instrument.
Figure 17:
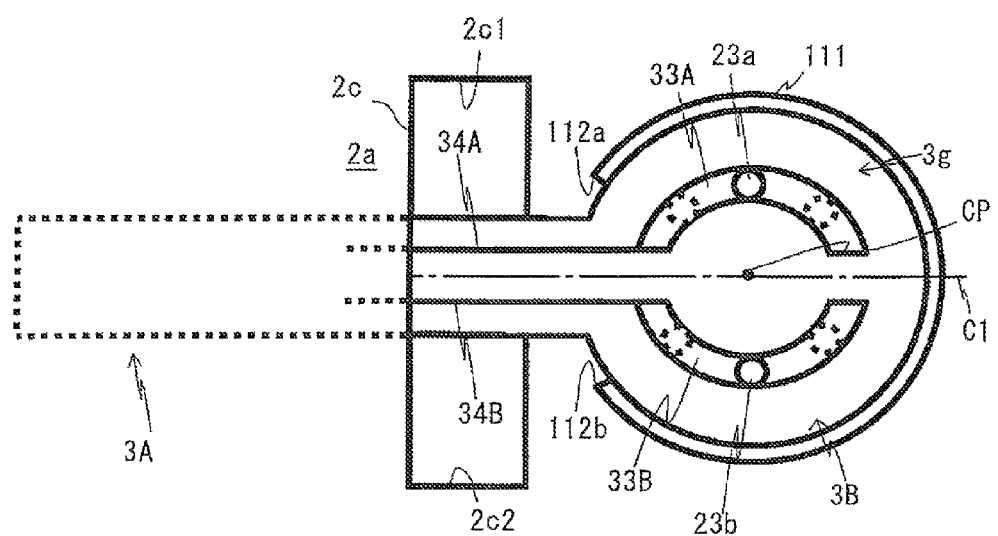
FIG. 17 is a view schematically showing a state where the glucose sensor attached to the monitoring instrument according to the sixth embodiment is viewed in plane from above.

FIG. 16 schematically illustrates a state in which the electrochemical sensor (a glucose sensor 3g) according to the sixth embodiment is attached to the monitoring instrument 2. FIG. 17 schematically shows a state where the glucose sensor 3g attached to the monitoring instrument 2 is viewed in plane from above.

As illustrated in FIG. 17, the glucose sensor 3g according to the sixth embodiment does not include the through-hole 35 formed in the glucose sensor 3 according to the first embodiment. An outer edge of the other end portion 3B of the glucose sensor 3g has a circular shape.

On the other hand, as illustrated in FIG. 16, a mounting portion 110 serving as an attaching target portion of the glucose sensor 3g is provided in a attaching position of the glucose sensor 3g on the upper surface of the base plate 2a. The mounting portion 110 includes a sidewall 111 erected on the upper surface of the base plate 2a. The sidewall 111 is formed in a cylindrical shape, of which a portion directed to the insertion port 2c is cut open, and has edges 112a, 112b.

An internal side surface of sidewall 111 is formed as a cylindrical peripheral face. An inside diameter of the sidewall 111 is formed in a way that matches with the outside diameter of the other end portion 3B of the glucose sensor 3g, and, in a state where the one end portion 3A of the glucose sensor 3g is located in a portion provided with none of the sidewall 111, the other end portion 3B is mounted on the upper surface (which is a bottom face 113 of the mounting portion 110) of the base plate 2a that is surrounded by the sidewall 111. Thereby, the glucose sensor 3g is attached to the monitoring instrument 2. At this time, such a state occurs that the central axis of the sidewall 111 is substantially coincident with the center CP of the other end portion 3B.

A distance longer than a width length of the glucose sensor 3g on the side of the one end portion 3A (which is the intermediate portion in the example of FIG. 17) is given between the edge 112a and the edge 112b, and the glucose sensor 3g is kept rotatable around the central axis of the sidewall 111 till contacting on one of the edges 112a, 112b. Herein, since the internal surface of the sidewall 111 has a shape corresponding to the outer edge shape of the other end portion 3B, the other end portion 3B rotates without misaligning the center of the other end portion 3B and the central axis of the sidewall 111. Accordingly, in the sixth embodiment, though any physical shaft is not provided, the glucose sensor 3g is enabled to swing (rotate) around the central axis defined by the sidewall 111 in the direction of the plane of the sensor. Then, each of the edges 112a, 112b of the sidewall 111 functions as the stopper to regulate the swing range of the glucose sensor 3g.

Except the constructive arrangement described above, the configurations of the glucose sensor 3g, the monitoring instrument 2 and the display unit 5 are the same as those in the first embodiment, and hence their descriptions are omitted. The sixth embodiment may acquire substantially the same operational effects as those in the first embodiment. It should be noted that the mounting portion 110 is constructed to have one sidewall 111 in the examples of FIGS. 16 and 17, however, a plurality of intermittently-provided sidewalls may form, on the whole, the cylindrical peripheral face for regulating an axle (a rocking shaft) of the other end portion 3B.

Seventh Embodiment

Next, a seventh embodiment of the present invention will be described. The seventh embodiment will discuss an example of another configuration for keeping a preferable state of the electric connection between the glucose sensor and the monitoring instrument 2. The seventh embodiment embraces the points that are common to the first embodiment, and hence the discussion will focus on different points in a way that omits the descriptions of the common points. Further, in the configurations of the glucose sensor and the monitoring instrument according to the seventh embodiment, the same components as those in the first embodiment are marked with the same numerals and symbols.

Figure 18A:
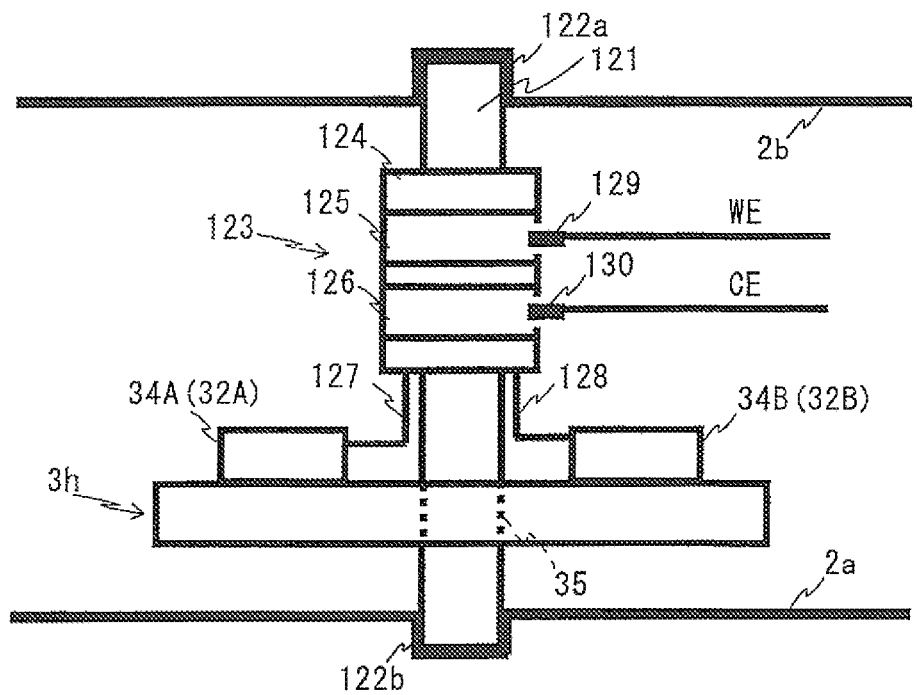
FIGS. 18A and 18B are views showing an example of applying a slip ring to an electric connection between the electrochemical sensor and the monitoring instrument.
Figure 18B:
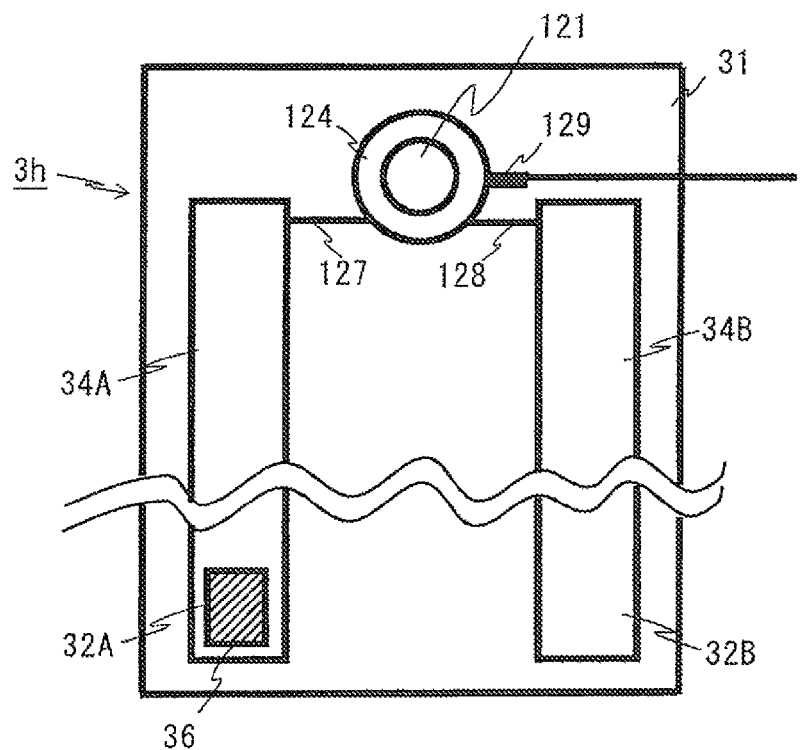

FIGS. 18A and 18B are views showing an example of applying a slip ring to the electric connection between the electrochemical sensor and the monitoring instrument. FIG. 18A schematically illustrates a state in which a principal portion for connecting the electrochemical sensor (the glucose sensor) fitted to the shaft to the monitoring instrument by use of the slip ring, is viewed sideways. FIG. 18B schematically shows a state in which the principal portion shown in FIG. 18(A) is viewed in plane from above.

As depicted in FIGS. 18A and 18B, an outer edge of a glucose sensor 3h according to the seventh embodiment is formed in a rectangular shape on the whole. Two strips of metal layers are formed substantially in parallel on one surface, defined as the electrode forming surface, of the base plate 31 configuring the glucose sensor 3h. The one metal layer is utilized for the working electrode 32A and the lead 34A, while the other metal layer is utilized for the counter electrode 32B and the lead 34B. A carbon layer is stacked on the portion used for the working electrode 32A, and the enzyme-immobilized layer 36 is further formed on this carbon layer.

As illustrated in FIG. 18A, similarly to the first embodiment, the through-hole 35 is formed in the other end portion 3B of, the glucose sensor 3h. The through-hole 35 receives the insertion of a shaft 121 erected within the housing for the monitoring instrument 2. The glucose sensor 3h is thereby attached to the monitoring instrument 2.

In the example shown in FIG. 18A, a lower end of the shaft 121 is inserted into a recessed portion 122a serving as a bearing formed in the upper surface of the base plate 2a, and an upper end of the shaft 121 is inserted into a recessed portion 122b serving as a bearing formed in the cover 2b. In the example illustrated in FIG. 18A, the shaft 121 is firmly fitted into the through-hole 35, and the shaft 121 integrally rotates according to swing of the glucose sensor 3h.

The shaft 121 is provided with a slip ring 123 for electrically connecting the lead portion 34A (the working electrode 32A) to the terminal WE of the potentiostat 62 (FIG. 4) and also electrically connecting the lead portion 34B (the counter electrode 32B) to the terminal CE of the potentiostat 62.

The slip ring 123 includes a cylindrical insulator 124 fixed to the shaft 121, two pieces of ring-shaped conductors 125, 126 provided over the external surface of the insulator 124 in the peripheral direction, and lead lines 127, 128 connected respectively to the conductors 125, 126 and extending outside from a lower part of the insulator 124 via the interior of the insulator 124. The respective lead lines 127, 128 are connected to the lead portions 34A, 34B by a known technique (e.g., by soldering). Therefore, the glucose sensor 3h is not provided with the contact pads.

The slip ring 123 further includes a brush 129 which always contacts on (comes into contact with) the conductor 125 and a brush 130 which always contacts on (comes into contact with) the conductor 126, in which the brush 129 is connected to the terminal WE, and the brush 130 is connected to the terminal CE.

With this arrangement, the working electrode 32A is connected to the terminal WE via the lead portion 34A, the lead line 127, the conductor 125 and the brush 129. On the other hand, the counter electrode 32B is connected to the terminal CE via the lead portion 34B, the lead line 128, the conductor 126 and the brush 130.

According to the configuration, even when the shaft 121 rotates due to the swing of the glucose sensor 3h, the brushes 129 and 130 continue to be in contact with the conductors 125 and 126. Therefore, the electric connection between the glucose sensor 3h and the monitoring instrument 2 is kept in a preferable state.

In the seventh embodiment, the glucose sensor 3h having a plate-like shape or a sheet-like shape is illustrated as an example. The glucose sensor 3h explained in the seventh embodiment may have a shape other than the plate-like shape or the sheet-like shape, for example, the glucose sensor 3h may be formed at a rod-like shape. The glucose sensor having the rod-like shape may have, for example, one of rod-like shapes disclosed at U.S. Pat. No. 7,460,898, No. 7,424,318, No. 7,467,003 and No. 7,366,556.

What is claimed is:

1. An electrochemical sensor comprising:
   a base plate including one end portion and another end portion;
   an electrode portion formed on the one end portion of the base plate;
   a connecting portion, formed on the another end portion of the base plate, for electrically connecting the electrode portion to a monitoring instrument; and
   an attaching portion formed on the another end portion, when the connecting portion is electrically connected to the monitoring instrument, the attaching portion being employed for attaching the another end portion to the monitoring instrument in a state where the one end portion that is not attached to the monitoring instrument is enabled to swing laterally relatively to the monitoring instrument by a substantial rotation of the another end portion attached to the monitoring instrument.

2. The electrochemical sensor according to claim 1, wherein
   the attaching portion includes a through-hole into which a shaft provided on the monitoring instrument is inserted, and
   the one end portion swings around the shaft.

3. The electrochemical sensor according to claim 1,
   wherein the attaching portion includes a notched portion formed in the another end portion of the base plate, and
   wherein the notched portion includes:
   a first portion having a diameter corresponding to an outside diameter of a shaft provided on the monitoring instrument; and
   a second portion communicating the first portion with an outer edge of the another end portion and having a gap that is smaller than the outside diameter of the shaft.

4. The electrochemical sensor according to claim 1,
   wherein the attaching portion includes two recessed portions formed coaxially in an electrode forming surface of the base plate and in a reverse surface to the electrode forming surface, and
   wherein respective ends of two shafts or protruded portions provided within the monitoring instrument and disposed in a face-to-face state on a same straight line are inserted into the two recessed portions when the electrochemical sensor is attached to the monitoring instrument.

5. The electrochemical sensor according to claim 1,
   wherein the attaching portion includes two protruded portions formed coaxially on an electrode forming surface of the base plate and on a reverse surface to the electrode forming surface, and
   wherein the respective protruded portions are inserted into two recessed portions provided within the monitoring instrument.

6. The electrochemical sensor according to claim 1,
   wherein the attaching portion includes;
   a recessed portion, formed on one of an electrode forming surface of the base plate and a reverse surface to the electrode forming surface, into which a protruded portion provided within the monitoring instrument is inserted; and
   a protruded portion formed, coaxially with the recessed portion, on another one of the electrode forming surface and the reverse surface and inserted into a recessed portion provided within the monitoring instrument.

7. The electrochemical sensor according to claim 1,
   wherein the attaching portion includes at least two through-holes, each of which has a circular arc shape, formed on a same circumference in the another end portion, and
   wherein at least two shafts provided within the monitoring instrument are inserted into the through-holes.

8. The electrochemical sensor according to claim 1,
   wherein the another end portion is formed in a circular shape and mounted on a mounting portion provided within the monitoring instrument, and
   wherein the mounting portion includes:
   a bottom face; and
   a sidewall erected from the bottom face and having a cylindrical peripheral face corresponding to the outside diameter of the another end portion.

9. The electrochemical sensor according to claim 1,
   wherein the connecting portion electrically connects the electrode portion to the monitoring instrument via a slip ring provided within the monitoring instrument.

10. A monitoring instrument attached with the electrochemical sensor according to claim 1, the monitoring instrument comprising:
    a monitoring-instrument-sided connecting portion to electrically connect the connecting portion to the monitoring instrument; and
    an attached portion to hold the another end portion in a state where the one end portion swings relatively to the monitoring instrument.

11. The monitoring instrument according to claim 10, wherein the attached portion includes a shaft to which the electrochemical sensor is attached, the shaft becoming a center of swing of the one end portion.

12. The monitoring instrument according to claim 10, wherein
    the attached portion includes two shafts or two protruded portions disposed in a face-to-face state on a same straight line, and
    ends of the shafts or the protruded portions are inserted respectively into two recessed portions formed coaxially in an electrode forming surface and in a reverse surface to the electrode forming surface of the electrochemical sensor.

13. The monitoring instrument according to claim 10, wherein the attached portion includes two recessed portions into which two protruded portions, which are formed coaxially on an electrode forming surface and on a reverse surface to the electrode forming surface of the electrochemical sensor, are inserted.

14. The monitoring instrument according to claim 10, wherein the attached portion includes:
- a protruded portion inserted into a recessed portion, which is formed on one of an electrode forming surface of the electrochemical sensor and a reverse surface to the electrode forming surface; and
- a recessed portion into which a protruded portion, which is formed, coaxially with the recessed portion, on another one of the electrode forming surface and the reverse surface, is inserted.

15. The monitoring instrument according to claim 10, wherein the attached portion includes at least two shafts inserted into at least two through-holes, each of which has circular arc shape, formed on a same circumference in the another end portion of the electrochemical sensor.

* * * * *